United States Patent [19]

Dørwald et al.

[11] Patent Number: 5,874,428
[45] Date of Patent: Feb. 23, 1999

[54] N-SUBSTITUTED AZA-HETEROCYCLIC CARBOXYLIC ACIDS AND ESTERS THEREOF

[75] Inventors: Florenzio Zaragossa Dørwald, Bagsvaerd; Knud Erik Andersen, Smørum; Rolf Hohlweg, Kvistgaard; Peter Madsen; Tine Krogh Jørgensen, both of Herlev; Uffe Bang Olsen, Vallensbaek; Henrik Sune Andersen, København; Svend Treppendahl, Virum, all of Denmark; Polivka Zdeněk, Prague, Czech Rep.; Silhánková Alexandra, Prague, Czech Rep.; Sindelár Karel, Prague, Czech Rep.

[73] Assignee: Novo Nordisk Als, Bagsvaerd, Denmark

[21] Appl. No.: 623,289

[22] Filed: Mar. 28, 1996

[30] Foreign Application Priority Data

| Apr. 7, 1995 | [DK] | Denmark | 0405/95 |
| Sep. 11, 1995 | [DK] | Denmark | 1005/95 |

[51] Int. Cl.⁶ .......................... A01N 43/46; C07D 223/18
[52] U.S. Cl. .............................. 514/217; 540/590
[58] Field of Search ................. 540/590; 514/217

[56] References Cited

U.S. PATENT DOCUMENTS

| 3,305,547 | 2/1967 | Stach et al. | 260/243 |
| 3,326,896 | 6/1967 | Holstius | 260/239 |
| 4,139,632 | 2/1979 | Hirose et al. | 544/46 |
| 5,595,989 | 1/1997 | Andersen et al. | 514/217 |

FOREIGN PATENT DOCUMENTS

| 9146676 | 11/1972 | Canada . |
| 1296519 | 5/1962 | France . |
| 830709 | 3/1960 | United Kingdom . |
| WO 95/18793 | 7/1995 | WIPO . |

OTHER PUBLICATIONS

Chemical Abstracts, vol. 76, No. 23, 5 Jun. 1972, Columbus, OH., p. 460, Abstract No. 140577n, JP, 7204069, A, Nakanishi, Michio et al., 4 Feb. 1972.

Chemical Abstracts, vol. 81, No. 5, 5 Aug. 1974, Columbus, OH., p. 424, Abstract No. 25566z, JP, 7330064, A, Nakanishi, Michio et al., 23 Dec. 1968.

Sindelar et al., "Anthistamine Substances. Tricyclic Analogues of N-(4,4-Diphenyl-3Butene-1-YL)Nipecotic Acid And Some Related Compounds." Collect. Azech. Chem. Commun., vol. 59(1994), pp. 667–674.

Katzung B.G., "Basic & Clinical Pharmacology", Sixth Edition, ©1995, p. 637.

Berthoud et. al., "Characteristics of Gastric & Pancreatic Responses . . . ", Chem. Abs., vol. 107(1987), p. 473, ABS# 75128j.

Delaney et.al., "Impaired Sensory Nerve Function . . . ", Chem. Abs., vol. 124 (1996), No. 5, p. 905, ABS# 52565m.

*Primary Examiner*—Mukund J. Shah
*Assistant Examiner*—Tamthom T. Ngo
*Attorney, Agent, or Firm*—Steve T. Zelson; James Harrington

[57] ABSTRACT

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

23 Claims, No Drawings

N-SUBSTITUTED AZA-HETEROCYCLIC CARBOXYLIC ACIDS AND ESTERS THEREOF

FIELD OF THE INVENTION

The present invention relates to novel N-substituted aza-heterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation. The invention also relates to the use of the present compounds for the treatment of insulin resistance in non-insulin-dependent diabetes mellitus (NIDDM) or aging, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastrointestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastro:intestinal diseases or migraine Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or aging-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or aging.

In U.S. Pat. No. 4,383,999 and No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

In addition to the above cited references, U.S. Pat. No. 3,074,953 discloses 1-(3-(10,11-dihydro-5H-dibenzo[a,d] cyclohepten-5-ylidene)-1-propyl)-4-phenyl-4-piperidinecarboxylic acid ethyl ester as a psychotropic drug. Analogous 1-substituted 4-phenyl-4-piperidinecarboxylic acid ester derivatives to the above cited compound are described (J. Med. Chem. 1967, 10, 627–635 and J. Org. Chem. 1962, 27, 230–240) as analgesics, antispasmodics and psychotropics. In JP 49032544, JP 48040357, FR 2121423, GB 1294550 and DE 2101066, 1-substituted 4-dialkylamino-4-piperidinecarboxamides are disclosed as psychotropic agents, for the treatment of schizophrenia and as inhibitors of inflammation.

DESCRIPTION OF THE INVENTION

The present invention relates to novel N-substituted aza-heterocyclic carboxylic acids and esters thereof of formula I

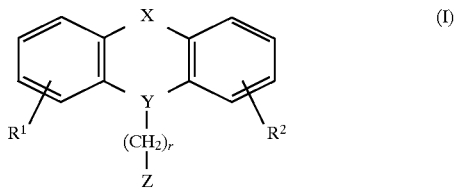

wherein $R^1$ and $R^2$ independently are hydrogen, halogen, trifluoromethyl, $NR^6R^7$, hydroxy, $C_{1-6}$-alkyl or $C_{1-6}$-alkoxy; and Y is >N̲—CH$_2$—, >C̲H—CH$_2$— or >C̲=CH— wherein only the underscored atom participates in the ring system; and X is —O—, —S—, —C(R$^6$R$^7$)—, —CH$_2$CH$_2$—, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N(R$^8$)—(C=O)—, —(C=O)—N(R$^8$)—, —O—CH$_2$—, —

CH$_2$—O—, —S—CH$_2$—, —CH$_2$—S—, —(C=O)—, —N(R$^9$)— or —(S=O)— wherein R$^6$, R$^7$, R$^8$ and R$^9$ independently are hydrogen or $C_{1-6}$-alkyl; and r is 1, 2 or 3; and Z is selected from

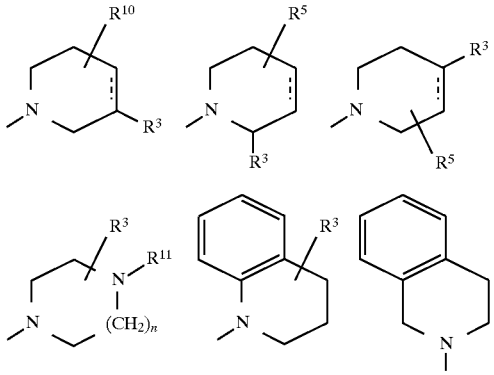

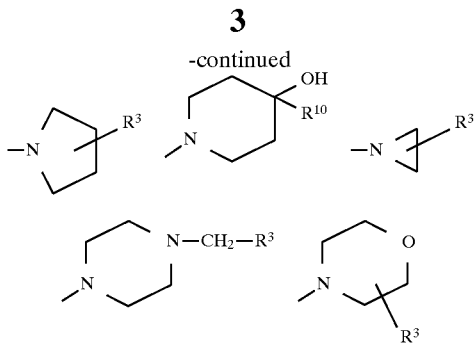

wherein n is 1 or 2; and $R^3$ is —$(CH_2)_m$OH or —$(CH_2)_p COR^4$ wherein m is 0, 1, 2, 3, 4, 5 or 6 and p is 0 or 1 and wherein $R^4$ is —OH, —$NH_2$, —NHOH or $C_{1-6}$-alkoxy; and $R^5$ is hydrogen, halogen, trifluoromethyl, hydroxy, $C_{1-6}$-alkyl or $C_{1-6}$-alkoxy; and $R^{10}$ is hydrogen, $C_{1-6}$-alkyl, $C_{1-6}$-alkoxy or phenyl optionally substituted with halogen, trifluoromethyl, hydroxy, $C_{1-6}$-alkyl or $C_{1-6}$-alkoxy; and $R^{11}$ is hydrogen or $C_{1-6}$-alkyl; and ... is optionally a single bond or a double bond; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tertbutyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

Illustrative examples of compounds encompassed by the present invention include:

1-(3-(10,11-Dihydro-5H-dibenz[b,f]azepin-5-yl)-1-propyl)-3-piperidinecarboxamide;

1-(3-(10,11-Dihydro-5H-dibenz[b,f]azepin-5-yl)-1-propyl)-4-piperidinecarboxylic acid;

1-(3-(10,11-Dihydro-5H-dibenz[b,f]azepin-5-yl)-1-propyl)-2-piperidinecarboxylic acid;

(1-(3-(10,11-Dihydro-5H-dibenz[b,f]azepin-5-yl)-1-propyl)-3-piperidinyl)methanol;

4-(4-Chlorophenyl)-1-(3-(10,11-dihydro-5H-dibenz[b,f]azepin-5-yl)-1-propyl)-4-piperidinol;

4-(3-(10,11-Dihydro-5H-dibenz[b,f]azepin-5-yl)-1-propyl)-2-piperazinecarboxylic acid;

(2S,4R)-1-(3-(10,11-Dihydro-5H-dibenz[b,f]azepin-5-yl)-1-propyl)-4-hydroxy-2-pyrrolidinecarboxylic acid;

4-(3-(10,11-Dihydro-5H-dibenz[b,f]azepin-5-yl)-1-propyl)-2-morpholinecarboxylic acid;

1-(3-(10,11-Dihydro-5H-dibenz[b,f]azepin-5-yl)-1-propyl)-2-aziridinecarboxylic acid;

2-(3-(10,11-Dihydro-5H-dibenz[b,f]azepin-5-yl)-1-propyl)-1,2,3,4-tetrahydro-4-isoquinolinecarboxylic acid;

1-(3-(10,11-Dihydro-5H-dibenz[b,f]azepin-5-yl)-1-propyl)-4-methyl-[1,4]-diazepane-6-caboxylic acid;

2-(3-(10,11-Dihydro-5H-dibenz[b,f]azepin-5-yl)-1-propyl)-1,2,3,4-tetrahydro-3-isoquinolinecarboxylic acid;

1-(3-(10,11-Dihydro-5H-dibenz[b,f]azepin-5-yl)-1-propyl)-3-piperidinecarboxylic acid hydroxamide;

(4-(3-(10,11-Dihydro-5H-dibenz[b,f]azepin-5-yl)-1-propyl)piperazin-1-yl)acetic acid;

1-(3-(10,11-Dihydro-5H-dibenz[b,f]azepin-5-yl)-1-propyl)-4-piperidineacetic acid;

1-(3-(10,11-Dihydro-5H-dibenzo[a,d]cyclohepten-5-ylidene)-1-propyl)-4-piperidinecarboxylic acid;

(R)-1-(3-(10,11-Dihydro-5H-dibenzo[a,d]cyclohepten-5-ylidene)-1-propyl)-3-piperidinecarboxamide;

(R)-1-(3-(10,11-Dihydro-5H-dibenzo[a,d]cyclohepten-5-ylidene)-1-propyl)-2-pyrrolidinecarboxylic acid;

(S)-1-(3-(10,11-Dihydro-5H-dibenzo[a,d]cyclohepten-5-ylidene)-1-propyl)-2-pyrrolidinecarboxylic acid;

(R)-1-(3-(10,11-Dihydro-5H-dibenzo[a,d]cyclohepten-5-ylidene)-1-propyl)-2-piperidinecarboxylic acid;

1-(3-(10H-Phenoxazin-10-yl)-1-propyl)-4-piperidinecarboxylic acid;

1-(3-(3-Chloro-10,11-dihydro-5H-dibenz[b,f]azepin-5-yl)-1-propyl)-4-piperidinecarboxylic acid;

1-(3-(10,11-Dihydro-5H-dibenz[b,f]azepin-5-yl)-1-propyl)-3-piperidineacetic acid;

1-(3-(10,11-Dihydro-5H-dibenz[b,f]azepin-5-yl)-1-propyl)-2-methyl-3-piperidinecarboxylic acid;

1-(3-(10,11-Dihydro-5H-dibenz[b,f]azepin-5-yl)-1-propyl)-3-quinuclidiniumcarboxylate;

1-(3-(2,8-Dibromo-10,11-dihydro-5H-dibenz[b,f]azepin-5-yl)-1-propyl)-4-piperidinecarboxylic acid;

1-(3-(3,7-Dichloro-10,11-dihydro-5H-dibenz[b,f]azepin-5-yl)-1-propyl)-4-piperidinecarboxylic acid;

1-(3-(3-Methyl-10,11-dihydro-5H-dibenzo[a,d]cyclohepten-5-ylidene)-4-piperidinecarboxylic acid;

1-(3-(3,7-Dimethyl-10,11-dihydro-5H-dibenz[b,f]azepin-5-yl)-1-propyl)-4-piperidinecarboxylic acid;

1-(3-(3-Dimethylamino-10,11-dihydro-5H-dibenz[b,f]azepin-5-yl)-1-propyl)-4-piperidinecarboxylic acid;

or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.:

Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as aging-associated obesity. Experimentally this has been demonstrated by the subcutaneous administration of glucose into ob/ob mice with or without previous oral treatment with a compound of general formula I.

The compounds of formula I may be prepared by the following method:

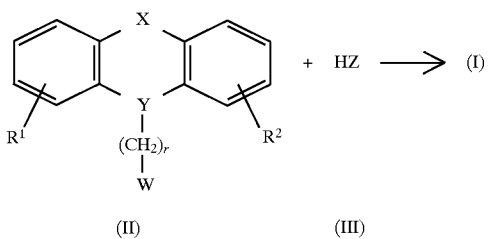

A compound of formula II wherein $R^1$, $R^2$, X, Y and r are as defined above and W is a suitable leaving group such as halogen, p-toluene sulphonate or mesylate may be reacted with an azaheterocyclic compound of formula III wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride and a catalyst, e.g. an alkali metal iodide at a temperature up to reflux temperature for the solvent used for e.g. 1 to 120 h. If esters have been prepared in which $R^4$ is alkoxy, compounds of formula I wherein $R^4$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

Pharmacological Methods
Formalin induced pain or paw oedema

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 $\mu$l 1% formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

REDUCED RELEASE OF CGRP ob/ob female mice, 16 weeks of age, where injected glucose (2g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of formalin induced pain response for some representative compounds are recorded in table 1.

TABLE 1

Inhibition of formalin induced pain response at 0.1 mg/kg

| Example no. | % Pain inhibition |
|---|---|
| 2 | 13 |
| 4 | 47 |
| 5 | 36 |
| 8 | 34 |
| 9 | 29 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| Mywacett ® 9-40 T approx. | 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography, $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm). M.p. is melting point and is given in °C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

1-(3-(10,11-Dihydro-5H-dibenz[b,f]azepin-5-yl)-1-propyl)-4-piperidinecarboxylic acid hydrochloride

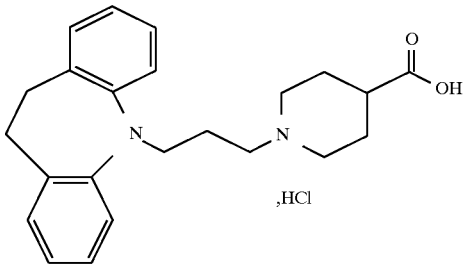

To a suspension of 10,11-dihydro-5H-dibenz[b,f]azepine (15.2 g, 0.078 mol) in toluene (100 ml), 3-chloropropionyl chloride (9.50 ml, 0.099 mol) was added, and the resulting mixture was heated at reflux temperature for 1 h. Saturated aqueous sodium bicarbonate (100 ml) was added, and the phases were separated. The organic phase was washed with brine (100 ml), dried ($MgSO_4$) and concentrated in vacuo. This afforded 23.6 g of 3-chloro-1-(10,11-dihydro-5H-dibenz[b,f]azepin-5-yl)-1-propanone as a solid which was used in the following step without further purification.

M.p. 107°–108° C.

Calculated for $C_{17}C_{16}ClNO$: C, 71.45%; H, 5.64%; N, 4.90%. Found: C, 71.45%; H, 5.79%; N, 5.01%.

To a solution of 3-chloro-1-(10,11-dihydro-5H-dibenz[b,f]azepin-5-yl)-1-propanone (14.0 g, 0.044 mol) in tetrahydrofuran (150 ml) at 0° C., sodium borohydride (6.66 g, 0.176 mol) was added, followed by dropwise addition of glacial acetic acid (10.0 ml). The resulting mixture was stirred at room temperature overnight and then heated at reflux temperature for 2 h. More sodium borohydride (6.50 g, 172 mmol) and then borontrifluoride diethyl etherate (20.0 ml, 0.163 mol) were added and heating at reflux temperature was continued for 20 h. Water (350 ml) was cautiously added and the phases were separated. The aqueous phase was extracted with toluene (3×100 ml). The combined organic phases were washed with brine (3×100 ml), dried ($MgSO_4$) and concentrated in vacuo. The residue was purified by flash chromatography on silica gel (100 g) using a gradient of heptane and ethyl acetate (10:0→10:2), to give 4.58 g (38%) of 5-(3-chloropropyl)-10,11-dihydro-5H-dibenz[b,f]azepine as an oil.

TLC: $R_f$=0.63 ($SiO_2$: ethyl acetate/heptane=1:2).

A mixture of 4-piperidinecarboxylic acid ethyl ester (2.55 g, 16.2 mmol), acetonitrile (13 ml), the above chloride (2.00 g, 0.0074 mol) and potassium iodide (1.14 g, 0.0068 mol) was heated at reflux temperature for 4 h and then stirred at room temperature overnight. Water (50 ml) was added and the product was extracted with ethyl acetate (3×20 ml). The combined organic extracts were washed with brine (2×20 ml), dried ($MgSO_4$) and concentrated in vacuo. The residue was purified by flash chromatography on silica gel using a gradient of heptane and ethyl acetate (10:1→1:1), to give 1.6 g (54%) of 1-(3-(10,11-dihydro-5H-dibenz[b,f]azepin-5-yl) -1-propyl)-4-piperidinecarboxylic acid ethyl ester as an oil.

TLC: $R_f$=0.26 ($SiO_2$: ethyl acetate/heptane =1:1).

Calculated for $C_{25}H_{32}N_2O_2$: C, 76.50%; H, 8.22%; N, 7.14%. Found: C, 76.34%; H, 8.51%; N, 6.88%.

The above ester (1.01 g, 2.57 mmol) was dissolved in ethanol (10 ml), and a solution of sodium hydroxide (0.59 g, 14.8 mmol) in water (1.5 ml) was added. The resulting mixture was stirred at room temperature for 3.5 h. A mixture of water (20 ml) and concentrated hydrochloric acid (3.0 ml) was added, and the aqueous phase was extracted with dichloromethane (3×15 ml). The combined organic extracts were washed with brine (20 ml) and dried (MgSO$_4$). Evaporation of the solvent gave a foam, which was redissolved in a mixture of methanol (1.0 ml) and ethyl acetate (5.0 ml). Concentration in vacuo afforded a solid, which was suspended in ethyl acetate (15 ml), heated at reflux temperature for 1 minute and allowed to cool to room temperature. The solid was filtered off and dried to give 0.9 g (88%) of the title compound as a powder.

Mp 195°–197° C.

Calculated. for $C_{23}H_{28}N_2O_2$, HCl: C, 68.90%; H, 7.29%; N, 6.99%. Found: C, 68.90%; H, 7.55%; N, 6.72%.

Example 2

4-(4-Chlorophenyl)-1-(3-(10,11-dihydro-5H-dibenz [b,f]azepin-5-yl)-1-propyl)piperidin-4-ol hydrochloride

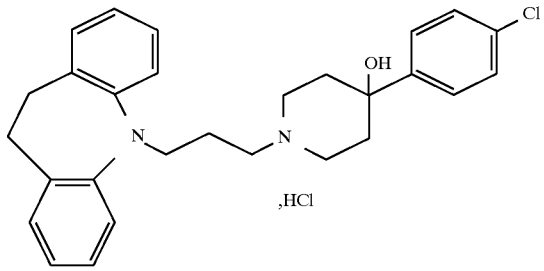

Ethyl malonyl chloride (25.0 g, 0.166 mol) was added to a suspension of 10,11-5 dihydro-5H-dibenz[b,f]azepine (27.6 g, 0.141 mol) in toluene (250 ml), and the resulting mixture was heated at reflux temperature for 1 h. Saturated, aqueous sodium bicarbonate (200 ml) was added, and the phases were separated. The organic phase was washed with brine (2×150 ml), dried (MgSO$_4$) and concentrated in vacuo. This afforded 56.0 g (100%) of 3-(10,11-dihydro-5H-dibenz[b,f] azepin-5-yl)-3-oxopropionic acid ethyl ester as an oil, which was used in the following step without further purification.

Lithium aluminum hydride (20.0 g, 0.527 mol) was introduced into a roundbottom flask under a nitrogen atmosphere. Toluene (800 ml) was added, followed by tetrahydrofuran (80 ml). The resulting suspension was cooled to 10–20° C. The above crude 3-oxopropionic acid ester was dissolved in tetrahydrofuran (250 ml) and slowly added dropwise. The addition rate was adjusted to assure that the temperature was kept at 10°–20° C. The resulting mixture was stirred at room temperature overnight. After cooling, 2N sodium hydroxide (200 ml) was added cautiously. Water (1.0 l) was added, the organic layer was decanted off and the aqueous phase was extracted with toluene (2×300 ml). The combined organic phases were washed with brine (2×100 ml), dried (MgSO$_4$) and concentrated in vacuo. The residue was purified by flash chromatography on silica gel (175 g) using a gradient of heptane and ethyl acetate (10:0→2:1), affording 21.2 g (59%) of 3-(10,11-dihydro-5H-dibenz-[b, f]azepin-5-yl)-1-propanol as an oil.

To a stirred solution of the above alcohol (1.01 g, 0.004 mol) and triethylamine (1.02 g, 0.010 mol) in toluene (25 ml) at 0° C., methanesulfonyl chloride (0.6 ml, 0.0077 mol) was added dropwise over 10 minutes. The resulting mixture was stirred at 0° C. for 1.5 h. Water (50 ml) was added and the phases were separated. The aqueous phase was extracted with toluene (50 ml), and the combined organic phases were washed with brine (2×50 ml), dried (MgSO$_4$) and concentrated in vacuo. The crude mesylate was mixed with 4-(4-chlorophenyl)piperidin-4-ol (0.81 g, 0.004 mol) and potassium carbonate (1.08 g, 0.008 mol) in acetonitrile (9 ml) and heated at reflux temperature for 6 h. The reaction mixture was left stirring at room temperature for 2 days. Water (50 ml) was added and the mixture was extracted with ethyl acetate (3×15 ml), washed with brine (2×20 ml), dried (MgSO$_4$) and concentrated in vacuo. Water (50 ml) was added and the mixture was acidified by addition of concentrated hydrochloric acid (3 ml). The aqueous solution was extracted with dichloromethane (2×20 ml), washed with brine (2×20 ml), dried (MgSO$_4$) and concentrated in vacuo. The resulting oil was dissolved in a mixture of ethyl acetate (15 ml) and methanol (2 ml). Heptane was added in small portions, just until the solution turned slightly turbid. After 4 h, crystals were filtered off, washed with heptane and dried, affording 1.1 g (61%) of the title compound as a solid.

M.p. 189°–191° C.

Calculated for $C_{28}H_{30}N_2O$, HCl: C, 69.56%; H, 6.67%; N, 5.79%; Found: C, 69.88%; H, 6.92%; N, 5.62%.

Example 3

1-(3-(10,11-Dihydro-5H-dibenz[b,f]azepin-5-yl)-1-propyl)-3-piperidinemethanol hydrochloride

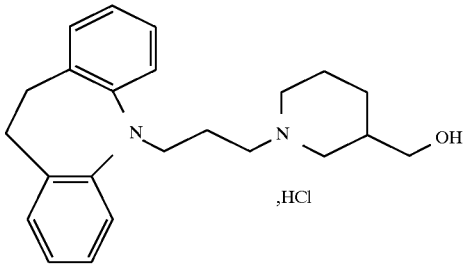

A mixture of 3-(hydroxymethyl)piperidine (1.01 g, 0.0088 mol), acetonitrile (9 ml), 5-(3-chloropropyl)-10,11-dihydro-5H-dibenzo[b,f]azepine (0.86 g, 0.003 mol. pre-pared similarly as described in example 1) and potassium iodide (0.56 g, 0.003 mol) was heated at reflux temperature for 18 h. Water (20 ml) was added, and the mixture was extracted with ethyl acetate (3×15 ml). The combined organic extracts were washed with brine (2×20 ml), dried (MgSO$_4$) and concentrated in vacuo. The residue was redissolved in a mixture of water (20 ml) and concentrated hydrochloric acid (3 ml), and extracted with dichloromethane (3×10 ml). The combined organic extracts were washed with brine (20 ml), dried (MgSO$_4$) and concentrated in vacuo. The residue was crystallised from a mixture of methanol (0.5 ml) and ethyl acetate (5 ml), affording 0.8 g (61%) of the title compound as needles.

M.p. 145°–147° C.

Calculated for $C_{23}H_{30}N_2O$, HCl: C, 71.39; H, 8.07; N, 7.24; Found: C, 71.15; H, 8.29; N, 7.01

Example 4

1-(3-(10,11-Dihydro-5H-dibenz[b,f]azepin-5-yl)-1-propyl)-3-piperidinecarboxamide hydrochloride

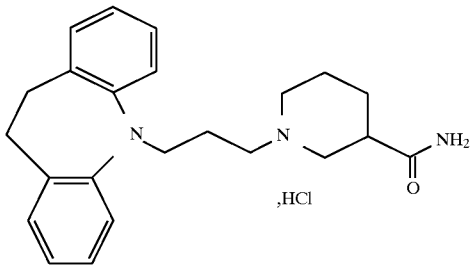

To a stirred solution of 3-(10,11-dihydro-5H-dibenz[b,f]azepin-5-yl)-1-propanol (1.44 g, 0.0057 mol, prepared similarly as described in example 2) and triethylamine (1.46 g, 0.014 mol) in toluene (40 ml) at 0° C., methanesulfonyl chloride (0.88 ml, 0.011 mol) was added dropwise over 10 minutes. The resulting mixture was stirred at 0° C. for 1.5 h. Toluene (50 ml) and water (100 ml) were added, and the phases were separated. The aqueous phase was extracted with toluene (50 ml), and the combined organic phases were washed with brine (2×100 ml), dried (MgSO$_4$) and concentrated in vacuo. The residue was dissolved in acetonitrile (20 ml) and 3-piperidinecarboxamide (1.09 g, 0.0085 mol) and potassium carbonate (1.76 g, 0.013 mol) were added. The mixture was heated at reflux temperature for 4 h, and stirred at room temperature for 40 h. Water (20 ml) was added, and the product was extracted with ethyl acetate (2×20 ml). The combined organic extracts were washed with brine (2×20 ml), dried (MgSO$_4$) and concentrated in vacuo. Water (20 ml) and concentrated hydrochloric acid (3.0 ml) were added, and the mixture was extracted with dichloromethane (2×20 ml), dried (MgSO$_4$) and concentrated in vacuo. The residue was redissolved in a mixture of warm ethyl acetate (10 ml) and methanol (1.0 ml), and after standing for 5 h at room temperature, a precipitate was filtered off and dried, affording 1.56 g (64 %) of the title compound.

HPLC retention time=20.44 minutes (5 μm C18 4×250 mm column, eluting with a 20–80% gradient of 0.1% trifluoroacetic acid/acetonitrile and 0.1% trifluoroacetic acid/water over 30 minutes at 35° C.)

Calculated for $C_{23}H_{29}N_3O$, HCl, 1.5 H$_2$O: C, 64.70%; H, 7.78%; N, 9.84%; Found: C, 65.13%; H, 7.85%; N, 9.85%.

Example 5

1-(3-(10,11-Dihydro-5H-dibenz[b,f]azepin-5-yl)-1-propyl)-2-piperidinecarboxylic acid hydrochloride

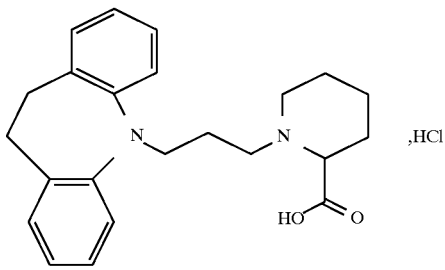

A mixture of 2-piperidinecarboxylic acid ethyl ester hydrochloride (0.60 g, 0.003 mol), acetonitrile (10 ml), 5-(3-chloropropyl)-10,11-dihydro-5H-dibenzo[b,f]azepine (0.60 g, 0.002 mol, prepared similarly as described in example 1), potassium iodide (0.40 g, 0.002 mol), potassium carbonate (1.03 g, 0.008 mol) and N,N-dimethylformamide (5 ml) was heated at reflux temperature for 85 h. Water (50 ml) was added, and the aqueous solution was extracted with ethyl acetate (3×20 ml). The combined organic extracts were washed with brine (2×50 ml), dried (MgSO$_4$) and concentrated in vacuo. The product was purified by column chromatography on silica gel (15 g) using a gradient of heptane and ethyl acetate (100:0→100:25), affording 0.83 g (97%) of 1-(3-(10,11-dihydro-5H-dibenz[b,f]azepin-5-yl)-1-propyl)-2-piperidinecarboxylic acid ethyl ester as an oil.

TLC: R$_f$=0.58 (SiO$_2$: heptane/ethyl acetate=1:1).

The above ester (0.83 g, 0.002 mol) was dissolved in a mixture of ethanol (8 ml), water (2 ml) and sodium hydroxide (0.58 g, 0.015 mol). The reaction mixture was stirred at room temperature for 50 h and at 50° C. for 5 h. Water (50 ml) and concentrated hydrochloric acid (3 ml) were added, and the resulting mixture was extracted with dichloromethane (3×10 ml). The combined organic extracts were washed with brine (2×20 ml), dried (MgSO$_4$) and concentrated in vacuo. The residue was re-dissolved in methanol (2 ml) and ethyl acetate (5 ml) and concentrated in vacuo. The solid residue was washed with a small amount of ethyl acetate and dried, affording 0.6 g (73%) of the title compound as a powder.

M.p. 122°–126° C.

Calculated for $C_{23}H_{28}N_2O_2$, HCl, 0.25 H$_2$O: C, 68.14%; H, 7.33%; N, 6.91%; Found: C, 68.34%; H, 7.63%; N, 6.66%.

Example 6

Potassium 4-(3-(10,11-dihydro-5H-dibenz[b,f]azepin-5-yl)-1-propyl)-2-piperazine-carboxylate

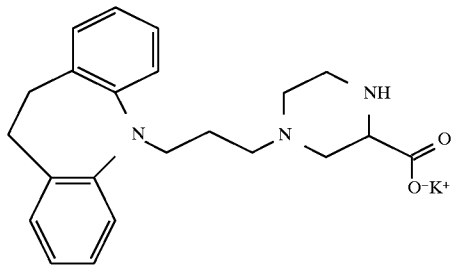

A mixture of 2-piperazinecarboxylic acid dihydrochloride (5.06 g, 0.025 mol), ethanol (100 ml) and concentrated sulphuric acid (6.0 ml) was heated at reflux temperature for 6 days. Toluene (10 ml) was added, and the resulting mixture was concentrated in vacuo to ⅔ of its original volume. Cold, saturated aqueous potassium carbonate (80 ml) was added and the mixture was extracted with toluene (3×100 ml). The combined organic extracts were washed with brine (30 ml), dried (MgSO$_4$) and concentrated in vacuo, affording 1.0 g (26%) of 2-piperazinecarboxylic acid ethyl ester as an oil. The oil crystallised upon standing at room temperature.

To a stirred solution of 3-(10,11 -dihydro-5H-dibenz[b,f]azepin-5-yl)-1-propanol (1.17 g, 0.0046 mol, prepared similarly as described in example 2) and triethylamine (1.18 g, 0.012 mol) in toluene (30 ml) at 0° C., methanesulfonyl chloride (0.70 ml, 0.009 mol) was added dropwise over 10 minutes. The resulting mixture was stirred at 0° C. for 1 h. Toluene (50 ml) and water (100 ml) were added, and the phases were separated. The aqueous layer was extracted with toluene (50 ml), and the combined organic phases were washed with brine (2×100 ml), dried (MgSO₄) and concentrated in vacuo. The residue was dissolved in acetonitrile (10 ml) and the above 2-piperazine-carboxylic acid ethyl ester (1.40 g, 0.0089 mol), potassium carbonate (0.67 g, 0.0049 mol) and toluene (5 ml) were added. The resulting mixture was heated at reflux temperature for 18 h. Water (50 ml) was added, and the mixture was extracted with ethyl acetate (3×20 ml). The combined organic extracts were washed with brine (2×20 ml), dried (MgSO₄) and concentrated in vacuo. The residue was purified by column chromatography on silica gel (27 g) using a gradient of methanol and ethyl acetate (5:100→20:100), affording 0.6 g (33%) of 4-(3-(10,11-dihydro-5H-dibenz[b,f]azepin-5-yl)-1-propyl)-2-piperazinecarboxylic acid ethyl ester as an oil.

TLC: R$_f$=0.60 (SiO₂: ethyl acetate/methanol=1:1).

A mixture of the above ester (0.55 g, 0.0014 mol), ethanol (5 ml), water (1 ml) and sodium hydroxide (0.34 g, 0.0085 mol) was stirred at room temperature for 18 h. Water (50 ml) and concentrated hydrochloric acid (3 ml) were added and the solution was washed with dichloromethane (4×15 ml). The dichloromethane extracts were discarded. The aqueous phase was made alkaline by addition of potassium carbonate (7.1 g) and the mixture was extracted with dichloromethane (4×15 ml). The combined organic extracts were washed with brine (20 ml), dried (MgSO₄) and concentrated in vacuo. This gave 0.6 g of an oil, which was triturated with acetonitrile (2 ml) and then dried in vacuo, affording 0.5 g (90%) of the title compound as a waxy solid.

M.p. 151°–155° C.

Calculated for C₂₂H₂₆N₃O₃K, 0.5 H₂O: C, 64.05%; H, 6.59%; N, 10.18%; Found: C, 64.34%; H, 7.04%; N, 10.16%.

Example 7

Sodium 4-(3-(10,11-dihydro-5H-dibenz[b,f]azepin-5-yl)-1-propyl)-1-piperazineacetate

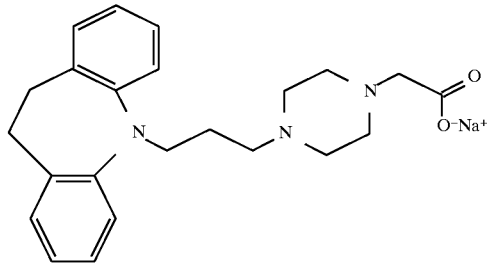

To a solution of 3-(10,11-dihydro-5H-dibenz[b,f]azepin-5-yl)-1-propanol (1.44 g, 0.0057 mol, prepared similarly as described in example 2) in dichloromethane (30 ml) at 0° C., triethylamine (1.73 g, 0.017 mol) was added followed by methanesulfonyl chloride (0.9 ml, 0.012 mol). The resulting mixture was stirred for 30 minutes at 0° C. Water (50 ml) was added, the phases were separated, and the organic layer was washed with brine (20 ml), dried (MgSO₄) and concentrated in vacuo. The residue was dissolved in acetonitrile (10 ml), N-(ethoxycarbonylmethyl)piperazine (2.44 g, 0.014 mol) was added and the reaction mixture was heated at 82° C. for 5.5 h. Water (50 ml) was added and the mixture was extracted with ethyl acetate (3×20 ml). The combined organic extracts were washed with brine (30 ml), dried (MgSO₄) and concentrated in vacuo. The residue was purified by column chromatography on silica gel (35 g) using ethyl acetate as eluent. This gave 1.5 g (63%) of 4-(3-(10, 11-dihydro-5H-dibenz[b,f]azepin-5-yl)-1-propyl)-1-piperazineacetic acid ethyl ester as an oil.

TLC: R$_f$=0.18 (SiO₂: ethyl acetate).

A mixture of the above ester (0.94 g, 0.0023 mol), ethanol (5 ml), water (1 ml) and sodium hydroxide (0.31 g, 0.0078 mol) was stirred at room temperature for 4.5 h. Water (50 ml) and concentrated hydrochloric acid (3 ml) were added and the solution was washed with dichloromethane (3×10 ml). The organic extracts were discarded. The aqueous phase was made alkaline by addition of 4N sodium hydroxide (20 ml) and potassium carbonate (4 g). The mixture was extracted with dichloromethane (5×20 ml), and the combined organic extracts were dried (MgSO₄) and concentrated in vacuo, affording 0.9 g of a foam. The foam was triturated and washed with ethyl acetate (2 ml), and dried in vacuo, affording 0.5 g (56%) of the title compound as a solid.

HPLC retention time=17.81 minutes (5 μm C18 4×250 mm column, eluting with a 20–80% gradient of 0.1% trifluoroacetic acid/acetonitrile and 0.1% trifluoroacetic acid/water over 30 minutes at 35° C.)

¹H NMR (400 MHz, CDCl₃) δ1.60 (m, 2H), 2.10–2.60 (m, 12H), 3.12 (bs, 4H), 3.68 (m, 2H), 6.83–7.17 (m, 8H).

Example 8

4-(3-(10,11-Dihydro-5H-dibenz[b,f]azepin-5-yl)-1-propyl)-2-morpholinecarboxylic acid hydrochloride

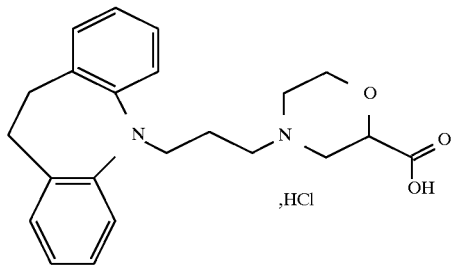

A mixture of 2-morpholinecarboxylic acid ethyl ester (0.50 g, 0.0031 mol, prepared similarly as described in Tetrahedron Letters, Volume 32, 2281–4, 1991), acetonitrile (6 ml), potassium carbonate (0.50 g, 0.0036 mol), potassium iodide (0.54 g, 0.0033 mol), methanesulfonic acid 3-(10,11-dihydro-5H-dibenz[b,f]azepin-5-yl)-1-propyl ester (0.36 g, 0.0011 mol, prepared similarly as described in example 2) and 5-(3-chloropropyl)-10,11-dihydro-5H-dibenz[b,f]azepine (0.40 g, 0.0015 mol, prepared similarly as described in example 1) was heated at reflux temperature for 22 h. Water (50 ml) was added, and the mixture was extracted with ethyl acetate (3×15 ml). The combined organic phases were washed with brine (20 ml), dried (MgSO₄) and concentrated in vacuo. The product was purified by column chromatography on silica gel (30 g) using a gradient of heptane and ethyl acetate (10:0→10:4). This gave 0.4 g (42%) of 4-(3-(10,11-dihydro-5H-dibenz[b,f]azepin-5-yl)-1-propyl)-2-morpholinecarboxylic acid ethyl ester as an oil.

TLC: R$_f$=0.33 (SiO₂: ethyl acetate/heptane=1:1).

A mixture of the above ester (0.40 g, 0.0010 mol), ethanol (10 ml) and 4N sodium hydroxide (2 ml) was stirred at room temperature for 17 h. Water (50 ml) and concentrated hydrochloric acid (3 ml) were added and the mixture was extracted with ethyl acetate (3×20 ml). The combined organic extracts were washed with brine (20 ml) and dried (MgSO₄). After filtering off the drying agent, a solid started to precipitate from the solution. After standing for 4 h at room temperature, the precipitate was filtered off, and the product was dried in vacuo. This gave 0.2 g (49%) of the title compound as a solid.

M.p. 196°–199° C.

Calculated for $C_{22}H_{26}N_2O_3$, HCl, 0.25 $H_2O$: C, 64.86%; H, 6.80%; N, 6.88%; Found: C, 65.12%; H, 7.09%; N, 6.39%.

Example 9

2-(3-(10,11-Dihydro-5H-dibenz[b,f]azepin-5-yl)-1-propyl)-1,2,3,4-tetrahydro-3-isoquinolinecarboxylic acid hydrochloride

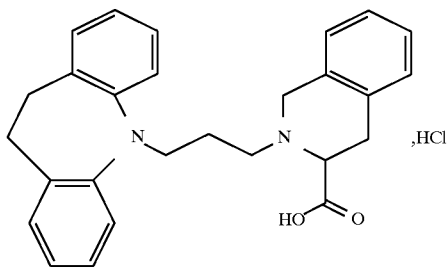

To a solution of 3-(10,11-dihydro-5H-dibenz[b,f]azepin-5-yl)-1-propanol (1.05 g, 0.0041 mol, prepared similarly as described in example 2) in dichloromethane (40 ml) at 0° C., triethylamine (1.28 g, 0.013 mol) was added, followed by methanesulfonyl chloride (0.9 ml, 0.012 mol). After stirring for 30 minutes at 0° C., water (50 ml) was added and the phases were separated. The organic layer was washed with brine (20 ml), dried ($MgSO_4$) and concentrated in vacuo. The residue was dissolved in acetonitrile (12 ml), and 1,2,3,4-tetrahydro-3-isoquinolinecarboxylic acid methyl ester (1.13 g, 0.0050 mol), N,N-dimethyl-formamide (5 ml), potassium carbonate (1.32 g, 0.0096 mol) and potassium iodide (0.30 g, 0.0018 mol) were added. The reaction mixture was heated at 82° C. for 12 h. N,N-Dimethylformamide (5 ml) was added and heating was continued for further 16 h. Water (50 ml) was added and the mixture was extracted with ethyl acetate (3×20 ml). The combined organic extracts were washed with brine (2×20 ml), dried ($MgSO_4$) and concentrated in vacuo. The product was purified by column chromatography on silica gel (80 g) using a gradient of heptane and ethyl acetate (10:0→10:3), affording 1.4 g (76%) of 2-(3-(10,11-dihydro-5H-dibenz[b,f]azepin-5-yl)-1-propyl)-1,2,3,4-tetrahydro-3-isoquinolinecarboxylic acid methyl ester as an oil.

TLC: $R_f$=0.61 ($SiO_2$: heptane/ethyl acetate=1:1).

A mixture of the above ester (0.80 g, 0.0019 mol), ethanol (5 ml), tetrahydrofuran (5 ml) and 4N sodium hydroxide (4 ml) was stirred at room temperature for 22 h. Water (50 ml) and concentrated hydrochloric acid (2 ml) were added and the mixture was extracted with ethyl acetate (2×20 ml). The combined organic extracts were washed with brine (10 ml), dried ($MgSO_4$) and concentrated in vacuo. This gave 0.8 g of a solid, which was triturated and washed with ethyl acetate (2×5 ml). Drying in vacuo, afforded 0.6 g (75%) of the title compound as a solid.

M.p. 205°–208° C.

Calculated for $C_{27}H_{28}N_2O_2$, HCl, 0.25 $H_2O$: C, 71.51%; H, 6.56%; N, 6.18%; Found: C, 71.34%; H, 6.69%; N, 5.90%.

Example 10

1-(3-(10,11-Dihydro-5H-dibenz[b,f]azepin-5-yl)-1-propyl)-4-piperidineacetic acid hydrochloride

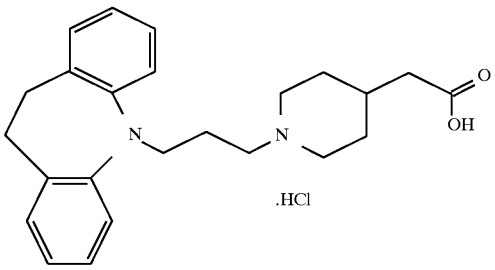

A mixture of 5-(3-chloropropyl)-10,11-dihydro-5H-dibenz[b,f]azepine (1.5 g, 0.0055 mol, prepared similarly as described in example 1) and potassium iodide (5.4 g, 0.0327 mol) in methyl ethyl ketone (100 ml) was heated at reflux temperature for 2.5 h. Potassium carbonate (1.5 g, 0.0109 mol) and 4-piperidineacetic acid ethyl ester (1.4 g, 0.0082 mmol, described in J. Am. Chem. Soc., Vol. 75, 6249, 1953) were added and the reaction mixture was stirred at 75° C. overnight. After cooling, the reaction mixture was filtered (Hyflo) and the solvent was evaporated in vacuo. The residue was purified by flash chromatography on silica gel (150 g) using a gradient of heptane and ethyl acetate (1:1→3:7), to give 0.6 g of 1-(3-(10,11-dihydro-5H-dibenz[b,f]-azepin-5-yl)-1-propyl)-4-piperidineacetic acid ethyl ester as an oil.

TLC: $R_f$=0.10 ($SiO_2$: ethyl acetate/heptane=1:1).

To a solution of the above ester (0.6 g, 0.0015 mol) in ethanol (5 ml) 4N sodium hydroxide (0.8 ml) was added and the mixture was stirred at room temperature for 2.5 h and then left in a freezer overnight. The cold reaction mixture was allowed to warm to room temperature during 1 h, and 4 N hydrochloric acid (1.2 ml) and water (10 ml) were added. The mixture was extracted with dichloromethane (2×100 ml). The combined organic extracts were dried ($MgSO_4$) and the solvent was evaporated in vacuo. The residue was reevaporated with a mixture of acetone and isopropyl acetate and then treated with a mixture of acetone and isopropyl acetate to give a solid which was isolated and dried in vacuo. This afforded 0.33 g of the title compound.

M.p. 185°–188° C.

Calculated. for $C_{24}H_{30}N_2O_2$, HCl: C, 69.47%; H, 7.53%; N, 6.75%. Found: C, 69.21%; H, 7.80%; N, 6.45%.

Example 11

1-(3-(10,11-Dihydro-5H-dibenzo[a,d]cyclohepten-5-ylidene)-1-propyl)-4-piperidinecarboxylic acid hydrochloride

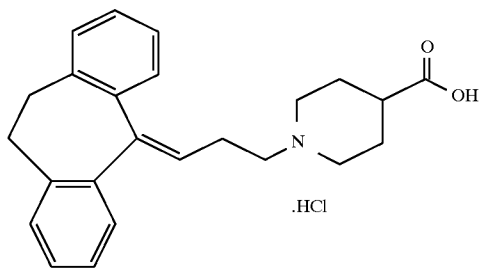

5-(3-Bromo-1-propylidene)-10,11-dihydro-5H-dibenzo[a,d]cycloheptene (3.00 g, 0.0096 mol), potassium carbonate (8.3 g, 0.060 mol), potassium iodide (3.3 g, 0.020 mol) and 4-piperidinecarboxylic acid ethyl ester (3.1 ml, 0.020 mol) was mixed in methyl ethyl ketone (100 ml) and heated at reflux temperature for 20 h and stirred at room temperature for 3 days. Water (100 ml) was added, the phases were separated, and the aqueous phase was extracted with ethyl acetate. The organic phase was dried ($MgSO_4$) and evaporated in vacuo to give the crude product in almost quantitative yield. The crude product was treated with 1N hydrochloric acid and ethyl acetate, evaporated to dryness and crystallised from ethyl acetate to give 2.89 g of 1-(3-(10,11-dihydro-5H-dibenzo[a,d]cyclohepten-5-ylidene)-1-propyl)-4-piperidinecarboxylic acid ethyl ester hydrochloride as a solid.

M.p. 169–170° C.

A mixture of the above ester (0.105 g, 0.27 mmol), ethanol (15 ml) and 1N sodium hydroxide (10 ml) was heated at reflux temperature for 3 h and then cooled to room temperature. Water (75 ml) was added, and the mixture was acidified with 5N hydrochloric acid and extracted with dichloromethane (3×75 ml), dried ($MgSO_4$) and evaporated in vacuo. The resulting foam was crystallised from acetone affording 0.080 g of the title compound as crystals.

M.p. 224–226° C.

Calculated. for $C_{24}H_{27}NO_2$, HCl: C, 72.44%; H, 7.09%; N, 3.52%. Found: C, 72.83%; H, 7.38%; N, 3.23%.

Example 12

(R)-1-(3-(10,11-Dihydro-5H-dibenzo[a,d]cyclohepten-5-ylidene)-1-propyl)-3-piperidinecarboxamide hydrochloride

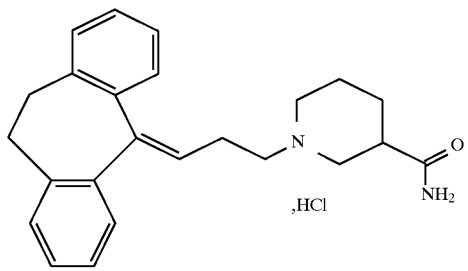

(R)

(R)-1-(3-(10,11-Dihydro-5H-dibenzo[a,d]cyclohepten-5-ylidene)-1-propyl)-3-piperidinecarboxylic acid hydrochloride (4.96 g, 12.5 mmol, prepared as described in WO 9518793) was dissolved in N,N-dimethylformamide (60 ml). N-Hydroxybenzotriazole (1.86 g, 13.8 mmol) and 1-ethyl-3-(3-dimethylamino-propyl)carbodiimide hydrochloride (2.64 g, 13.8 mmol) were added, and the resulting mixture was stirred at room temperature for 20 minutes. Ammonium hydrogencarbonate (1.98 g, 25 mmol) was added and the mixture was stirred 1 day at room temperature. Ethyl acetate (200 ml) was added and the resulting mixture was extracted with water (200 ml), 5% aqueous citric acid (200 ml), and saturated sodium hydrogencarbonate (200 ml). The combined aqueous phases were evaporated to dryness in vacuo and the residue was extracted with dichloromethane (200 ml). The resulting dichloromethane suspension was filtered and evaporated. The residue was purified by column chromatography on silica gel (600 ml) using a mixture of ethyl acetate and triethyl amine (95:5) as eluent. This afforded 1.92 g (43%) of the free base as an oil, which was converted to the hydrochloride by dissolution in diethyl ether (25 ml) and addition of 1N hydrochloric acid in diethyl ether (5.9 ml). Filtration followed by drying in vacuo, afforded 1.53 g, (31%) of the title compound as a solid.

TLC: $R_f$=0.33 ($SiO_2$: Ethyl acetate/triethylamine=95:5).

$^1$H NMR (400 MHz, $CDCl_3$): δ1.38 (dq, 1H), 1.75–1.97 (m, 3H), 2.5–3.7 (m, 13H), 5.78 (t, 1H), 7.0–7.3 (m, 8H), 7.63 (s, 1H), 10.8 (s, 1H).

M.p. >250° C.

Calculated for $C_{24}H_{28}N_2O$, HCl: C, 72.62%; H, 7.36%; N, 7.06%; Found: C, 72.24%; H, 7.59%; N, 6.87%.

Example 13

(R)-1-(3-(10,11-Dihydro-5H-dibenzo[a,d]cyclohepten-5-ylidene)-1-propyl)-2-pyrrolidinecarboxylic acid hydrochloride

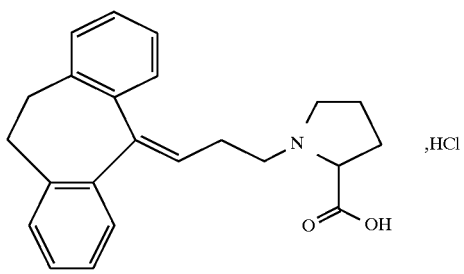

(R)

5-(3-Bromo-1-propylidene)-10,11-dihydro-5H-dibenzo[a,d]cycloheptene (3.86 g, 12.3 mmol, prepared as described in WO 9518793), potassium carbonate (10.2 g, 74 mmol), potassium iodide (4.08 g, 24.6 mmol), and D-proline methyl ester hydrochloride (2.45 g, 14.8 mmol) were mixed in methyl ethyl ketone (40 ml) and heated at reflux temperature for 20 h. After cooling, the mixture was filtered and the filtrate was evaporated in vacuo. The residue was purified by column chromatography on silica gel (800 ml) using a mixture of ethyl acetate and heptane (1:3) as eluent. This afforded 0.96 g (22%) of (R)-1-(3-(10,11-dihydro-5H-dibenzo[a,d]cyclohepten-5-ylidene)-1-propyl)-2-pyrrolidinecarboxylic acid methyl ester as an oil.

TLC: $R_f$=0.39 ($SiO_2$: ethyl acetate/heptane=1:2).

The above ester was dissolved in 1,4-dioxane (40 ml), and water (5 ml) was added. 1N Aqueous sodium hydroxide (2.15 ml) was added in portions at room temperature over 6 h. The mixture was stirred overnight at room temperature. 1 N Aqueous sodium hydroxide (0.84 ml) was added in portions over 20 h. Water (100 ml) was added and the mixture was washed with diethyl ether (2×100 ml). The aqueous phase was acidified to pH=2 with 1N hydrochloric acid and extracted with dichloromethane (2×100 ml). The combined organic extracts were dried ($MgSO_4$) and evaporated in vacuo to give 0.29 g (41%) of the title compound as an amorphous solid.

$^1$H-NMR (400 MHz, $CDCl_3$): δ1.95 (bs, 2H), 2.3 (m, 2H), 2.5–3.4 (m, 11 H), 5.78 (t,1H), 7.0–7.3 (m, 8H).

Calculated for $C_{23}H_{25}NO_2$, HCl: C, 71.96 %; H, 6.83 %; N, 3.65 %, Found: C, 72.15 %; H, 7.37 %; N, 3,40 %.

EXAMPLE 14

(S)-1-(3-(10,11-Dihydro-5H-dibenzo[a,d]cyclohepten-5-ylidene)-1-propyl)-2-pyrrolidinecarboxylic acid hydrochloride

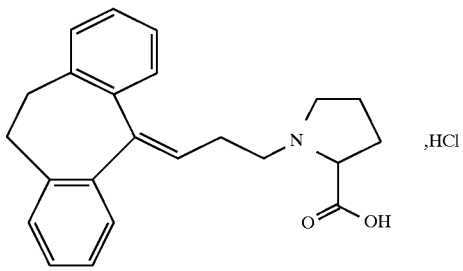

5-(3-Bromo-1-propylidene)-10,11-dihydro-5H-dibenzo[a,d]cycloheptene (2.00 g, 6.4 mmol, prepared as described in WO 9518793), potassium carbonate (5.3 g, 38.4 mmol), potassium iodide (2.12 g, 12.8 mmol), and L-proline methyl ester hydrochloride (1.27 g, 7.7 mmol) were mixed in methyl ethyl ketone (40 ml) and heated at reflux temperature for 12 h. After cooling, the mixture was filtered, and the filtrate was evaporated. The residue was purified by column chromatography on silica gel (800 ml) using a mixture of ethyl acetate and heptane (1:2) as eluent. This afforded 1.64 g (71 %) of (S)-1-(3-(10,11-dihydro-5H-dibenzo[a,d]cyclohepten-5-ylidene)-1-propyl)-2-pyrrolidinecarboxylic acid methyl ester as an oil.

TLC: $R_f$=0.39 (SiO$_2$: ethyl acetate/heptane=1:2)

The above ester (1.3 g, 3.6 mmol) was dissolved in 1,4-dioxane (50 ml), and water (5 ml) was added. 1 N Aqueous sodium hydroxide (3.8 ml) was added in portions at room temperature over 6 h. The mixture was stirred overnight at room temperature. Water (100 ml) was added and the mixture was washed with diethyl ether (2×100 ml). The aqueous phase was acidified to pH=2 with 1 N hydrochloric acid and extracted with dichloromethane (2×100 ml). The combined organic extracts were dried (MgSO$_4$) and evaporated in vacuo to give 0.80 g (58 %) of the title compound as an amorphous solid.

$^1$H-NMR (400 MHz, CDCl$_3$): δ 1.95 (bs, 2H), 2.3 (m, 2H), 2.5–3.4 (m, 11H), 5.78 (t, 1H), 7.0–7.3 (m, 8H).

Calculated for C$_{23}$H$_{25}$NO$_2$, HCl: C, 71.96 %; H, 6.83 %; N, 3.65 %; Found: C, 72.61 %; H, 7.30 %; N, 3.34 %.

Example 15

1-(3-(10,11-Dihydro-5H-dibenzo[a,d]cyclohepten-5-ylidene)-1-propyl)-2-piperidinecarboxylic acid hydrochloride.

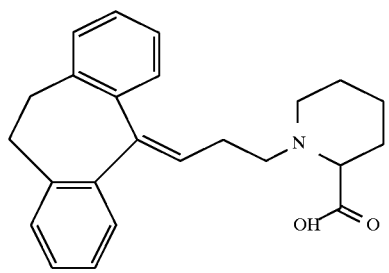

5-(3-Bromo-1-propylidene)-10,11-dihydro-5H-dibenzo[a,d]cycloheptene (10.0 g, 22 mmol, prepared as described in WO 9518793), potassium carbonate (18.24 g, 132 mmol), and DL-pipecolinic acid ethyl ester hydrochloride (5.40 g, 26 mmol) were mixed in ethyl acetate (50 ml) and heated at reflux temperature for 16 h. Additional potassium carbonate (10 g), DL-pipecolinic acid ethyl ester hydrochloride (2 g), and ethyl acetate (50 ml) were added and the mixture was heated at reflux temperature for 24 h. After cooling, the mixture was filtered, and the filtrate was evaporated. The residue was purified by column chromatography on silica gel (500 ml), eluting first with dichloromethane, and then with ethyl acetate. This afforded 7.92 g (92 %) of 1-(3-(10,11-dihydro-5H-dibenzo[a,d]cyclohepten-5-ylidene)-1-propyl)-2-piperidine carboxylic acid ethyl ester as an oil.

TLC: $R_f$=0.54 (SiO$_2$: ethyl acetate/heptane=3:7)

1N Hydrochloric acid (100 ml) was added to the above ester (7.7 g, 20 mmol) and the mixture was heated for 1 h while water and ethanol was distilled off (20 ml distilled). Water (40 ml) was added and the mixture was heated for 5 h while water and ethanol was distilled off. After cooling, toluene (100 ml) was added to the mixture. The precipitated crystals were isolated by filtration and washed with 1N hydrochloric acid, affording the crude product (5.3 g). A portion of this (2.0 g) was further purified by dissolution in water (100 ml, 75° C.) and addition of 37 % hydrochloric acid (6 ml). The mixture was allowed to cool to room temperature. Filtration, washing with 1 N hydrochloric acid and drying in vacuo afforded 1.72 g of the title compound as a solid.

M.p. 126°–127 ° C.

$^1$H NMR (300 MHz, CDCl$_3$): δ 1.5–1.75 (m, 4H), 2.1 (m, 1H), 2.5–3.5 (m, 11H), 4.10 (bs, 1H), 5.80 (t, 1H), 7.05–7.23 (m, 8H).

Calculated for C$_{23}$H$_{26}$NO$_2$, HCl, 0.5 H$_2$O: C, 70.13 %; H, 7.16 %; N, 3.56 %, Found: C, 69.74 %; H, 7.46 %; N, 3.08 %.

Example 16

1-(3-(10H-Phenoxazin-10-yl)-1-propyl)-4-piperidinecarboxylic acid hydrochloride.

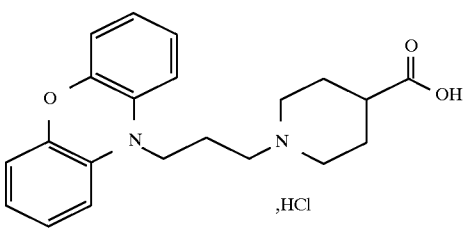

Phenoxazine (10.0 g, 54.6 mmol) was dissolved in N,N-dimethylformamide (300 ml) under a nitrogen atmosphere. Sodium hydride (3.27 g, 81.9 mmol, 60 % dispersion in oil) was added in portions, and the resulting mixture was stirred for 20 minutes at room temperature. Dropwise, 1-bromo-3-chloro-propane (21.48 g, 0.136 mmol) was added. The mixture was stirred overnight. Ammoniumchloride (5.5 g, 0.10 mol) was added over 4 minutes and stirring was continued for 30 minutes. The mixture was poured into water (800 ml) and extracted with dichloromethane (2×600 ml). The combined organic extracts were dried (MgSO$_4$) and evaporated in vacuo. This afforded 16.0 g crude 10-(3-chloropropyl)-10H-phenoxazine.

The above crude chloride (5.09 g, 17.4 mmol) was dissolved in acetonitrile (100 ml) and potassium iodide (2.74 g, 16.5 mmol) was added. 4-Piperidinecarboxylic acid ethyl ester (6.00 g, 38.2 mmol) was dissolved in acetonitrile (30 ml) and added. The resulting mixture was heated at reflux temperature for 24 h and left stirring at room temperature for 48 h. Water (100 ml) was added followed by ethyl acetate (100 ml). The aqueous phase was extracted with ethyl acetate (3×100 ml), and the combined organic phases were washed with brine (2×100 ml) and dried (MgSO$_4$). After evaporation in vacuo, the residue was purified by column chromatography on silica gel (500 ml) using a mixture of heptane and ethyl acetate (1:1) as eluent. This afforded 5.18 g (77 %) of 1-(3-(10H-phenoxazin-10-yl)-1-propyl)-4-piperidinecarboxylic acid ethyl ester as an oil.

TLC: R$_f$=0.2 (SiO$_2$: ethyl acetate/heptane=1:1)

The above ester (1.56 g, 4.04 mmol) was dissolved in a mixture of 96% ethanol (20 ml) and tetrahydrofuran (20 ml). A solution of sodium hydroxide (0.95 g) in water (3 ml) was added, and the reaction mixture was stirred at room temperature for 1.5 h. 0.1M Hydrochloric acid (28 ml) was added and the mixture was extracted with dichloromethane (3×30 ml). The combined organic extracts were washed with brine (30 ml), dried (MgSO$_4$) and evaporated in vacuo. Twice, acetone was added and the solution was evaporated in vacuo. After a third addition of acetone, precipitation started, and the mixture was left stirring 2 h. After filtration, the solid was re-suspended in acetone (25 ml) and left stirring overnight. The solid was filtered off, washed with acetone and dried. This afforded 1.30 g (83%) of the title compound as a solid.

M.p. 196°–198° C.

Calculated for C$_{21}$H$_{24}$N$_2$O$_3$, HCl: C, 64.86%; H, 6.48%; N, 7.20%, Found: C, 64.82%; H, 6.78%; N, 6.77%.

Example 17

1-(3-(3-Chloro-10,11-dihydro-5H-dibenz[b,f]azepin-5-yl)-1-propyl)-4-piperidinecarboxylic acid hydrochloride.

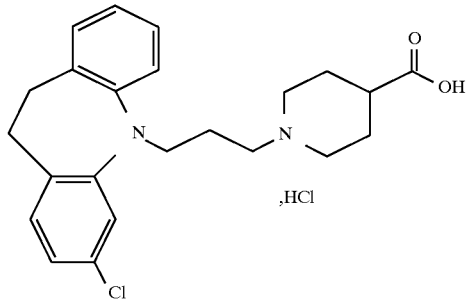

3-Chloro-10,11-dihydro-5H-dibenz[b,f]azepine (3.82 g, 16.6 mmol) was dissolved in toluene (20 ml). A solution of 3-chloropropionylchloride (2.53 g, 19.9 mmol) in toluene was added dropwise, and the resulting mixture was heated to 95° C. and stirred at that temperature for 30 minutes. The mixture was stirred overnight at room temperature. Further 3-chloropropionylchloride (2.53 g, 19.9 mmol) was added and the mixture was stirred at 95° C. for 1.5 h. After cooling, 0.2M sodium hydroxide (10 ml) was added, and the phases were separated. The organic phase was diluted with more toluene (50 ml); and washed with first 0.2M sodium hydroxide (6×10 ml) and then with more 0.2M sodium hydroxide (3×20 ml) until the aqueous phase was alkaline. The organic phase was washed with water (3×15 ml), brine (25 ml), and dried (MgSO$_4$). Evaporation in vacuo afforded 5.23 g (98%) of crude 3-chloro-1-(3-chloro-10,11-dihydro-5H-dibenz[b,f]azepin-5-yl)-1-propanone as an oil. This was further purified by addition of a mixture of heptane and ethyl acetate (1:1). This afforded 3.14 g (59%) of the product as a solid.

A 1.0M solution of lithiumaluminium hydride in tetrahydrofuran (18.7 ml, 18.7 mmol) was introduced into a 250 ml dry, three-necked, roundbottom flask under a nitrogen atmosphere. The solution was cooled on an icebath. Concentrated sulphuric acid (0.5 ml) was added dropwise, with caution, over 10 minutes. More dry tetrahydrofuran (20 ml) was added to compensate for evaporated solvent and the mixture was stirred for 15 minutes. Additional tetrahydrofuran was added (20 ml) and the icebath was removed. The mixture was stirred for 75 minutes at room temperature. The above amide (3.0 g, 9.3 mmol) was dissolved in dry tetrahydrofuran (25 ml) and dropwise added over 20 minutes. The reaction mixture was stirred for 1 h. Water (0.7 ml) was added, followed subsequently by 4N sodium hydroxide (0.7 ml) and water (2.1 ml). Stirring was continued for 30 minutes. The mixture was filtered (hyflo) and evaporated in vacuo, affording 2.70 g (95%) 3-chloro-5-(3-chloropropyl)-10,11-dihydro-5H-dibenz[b,]azepine as an oil.

The above chloride (1.50 g, 4.91 mmol) was dissolved in acetonitrile (10 ml), and a solution of 4-piperidinecarboxylic acid ethyl ester (1.70 g, 10.8 mmol) in acetonitrile (4 ml) was added, followed by potassium iodide (0.76 g, 4.6 mmol). The resulting mixture was heated at reflux temperature for 24 h. Water (50 ml) was added followed by ethyl acetate (50 ml). The aqueous phase was extracted with ethyl acetate (3×30 ml), and the combined organic phases were washed with brine (2×25 ml) and dried (MgSO$_4$). After evaporation in vacuo, the residue was purified by column chromatography on silica gel (150 ml) using a mixture of heptane and ethyl acetate (1:1) as eluent. This afforded 1.78 g (85 %) of 1-(3-(3-chloro-10,11-dihydro-5H-dibenz[b,f]azepin-5-yl)-1-propyl)-4-piperidinecarboxylic acid ethyl ester as an oil.

TLC: R$_f$=0.21 (SiO$_2$: ethyl acetate/heptane=1:1)

The above ester (1.70 g, 3.98 mmol) was dissolved in 99% ethanol (20 ml). A solution of sodium hydroxide (0.92 g) in water (2.5 ml) was added, and the reaction mixture was stirred at room temperature for 1 h. 1N Hydrochloric acid (23 ml) was added and the mixture was extracted with dichloromethane (3×25 ml). The combined organic extracts were washed with brine (25 ml) and water (20 ml), dried (MgSO$_4$) and evaporated in vacuo. Dichloromethane was added and the solution was re-evaporated. Isopropyl acetate was added to the resulting foam, and the precipitated solid was filtered off and dried. This afforded 1.28 g (74%) of the crude title compound. The product was redissolved in isopropanol, the solution was decanted and evaporated in vacuo. Dichloromethane was added and the solution was evaporated in vacuo. Isopropyl acetate was added to the resulting foam, and the precipitated solid was filtered off and dried. This procedure was repeated once more.

MS(EI) 398 (M$^+$-HCl, 18%).

HPLC retention time=24.14 minutes (5 μm C18 4×250 mm column, eluting with a 20–80% gradient of 0.1% trifluoroacetic acid/acetonitrile and 0.1% trifluoroacetic acid/water over 30 minutes at 35° C.)

Example 18

1-(3-(10,11-Dihydro-5H-dibenz[b,]azepin-5-yl)-1-propyl)-3-piperidineacetic acid hydrochloride

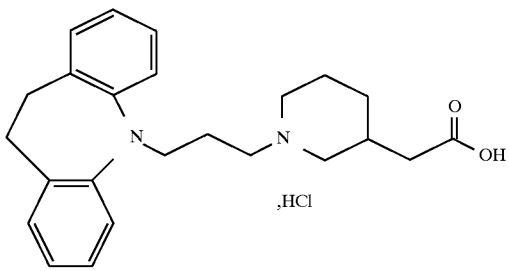

A suspension of 3-piperidineacetic acid (4.5 g, 0.032 mol, described in *J. Org. Chem.*, 28, 602, 1963) in a mixture of dry hydrogen chloride (excess) in ethanol was stirred at ambient temperature. When the solid was dissolved, the solution was stirred for 2 days. The solvent was evaporated in vacuo and the residue was reevaporated with diethyl ether (25 ml) and then stirred with diethyl ether (35 ml) for 20 minutes. The solid was isolated by filtration and dried. This afforded 6.1 g of 3-piperidineacetic acid ethyl ester hydrochloride as a solid.

M.p. 111°–113° C.

A mixture of potassium iodide (19.2 g, 0.12 mol) and methyl ethyl ketone (180 ml) was heated at reflux temperature for 1 h. A solution of 5-(3-chloropropyl)-10,11-dihydro-5H-dibenz[b,f]azepine (5.2 g, 0.019 mol, prepared similarly as described in example 1) in methyl ethyl ketone (25 ml) was added and heating at reflux temperature was continued for 3 h. Potassium carbonate (9.3 g, 0.067 mol) and 3-piperidineacetic acid ethyl ester hydrochloride (5.6 g, 0.027 mol) were added and the reaction mixture was heated at reflux temperature for 2 h. The temperature was lowered to just below reflux and the mixture was left with stirring overnight. After cooling, the reaction mixture was filtered (Hyflo) and the solvent was evaporated in vacuo. The residue was purified by flash chromatography on silica gel (225 g) using a mixture of heptane and ethyl acetate (1:1) as eluent, to give 5.0 g of 1-(3-(10,11-dihydro-5H-dibenz[b,f]-azepin-5-yl)-1-propyl)-3-piperidine-acetic acid ethyl ester as an oil.

TLC: $R_f$=0.19 (SiO$_2$: ethyl acetate/heptane=1:1).

To a solution of the above ester (2.5 g, 0.0062 mol) in ethanol (10 ml), 4N sodium hydroxide (2.3 ml) was added and the mixture was stirred at room temperature for 3 h. 4N Hydrochloric acid (3.8 ml) and water (10 ml) were added. The mixture was extracted with dichloromethane (2×250 ml). The combined organic extracts were dried (MgSO$_4$) and the solvent was evaporated in vacuo. The residue was reevaporated twice with acetone and stirred with acetone for a while. The solid was isolated by filtration and dried. This afforded 2.4 g of the title compound as a solid.

M.p. 233°–235° C.

Calculated. for $C_{24}H_{30}N_2O_2$, HCl: C, 69.47%; H, 7.53%; N, 6.75%. Found: C, 69.59%; H, 7.78%; N, 6.50%.

Example 19

1-(3-(10,11-Dihydro-5H-dibenz[b,f]azepin-5-yl)-1-propyl)-2-methyl-3-piperidinecarboxylic acid hydrochloride

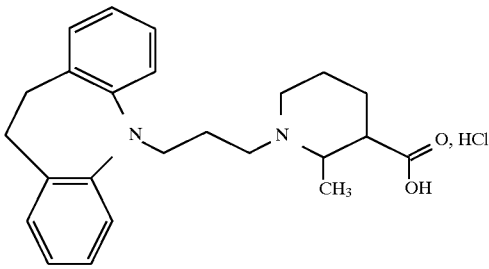

2-Methylnicotinic acid methyl ester (4.0 g, 0.026 mol) was dissolved in 1N hydrochloric acid (30 ml) and 10% palladium on carbon (0.8 g) was added. The resulting mixture was hydrogenated at 200 psi for 10 days. The reaction mixture was filtered and the solid was washed with dichloromethane (100 ml) and water (50 ml). The combined filtrates were evaporated in vacuo to give a residue which was reevaporated with dichloromethane (2×30 ml). This afforded 5.1 g of crude 2-methyl-3-piperidinecarboxylic acid methyl ester hydrochloride which was used for further reaction without purification.

A mixture of potassium iodide (17.5 g, 0.11 mol) and methyl ethyl ketone (180 ml) was heated at reflux temperature for 1 h. A solution of 5-(3-chloropropyl)-10,11-dihydro-5H-dibenz[b,f]azepine (4.8 g, 0.019 mol, prepared similarly as described in example 1) in methyl ethyl ketone (25 ml) was added and heating at reflux temperature was continued for 2 h. Potassium carbonate (8.5 g, 0.061 mol) and 2-methyl-3-piperidinecarboxylic acid methyl ester hydrochloride (5.1 g, 0.026 mol) were added and the reaction mixture was heated just below reflux temperature for 64 h. After cooling, the reaction mixture was filtered (Hyflo) and the solvent was evaporated in vacuo. The residue was purified by flash chromatography on silica gel (275 g) using a mixture of heptane and ethyl acetate (1:1) as eluent, to give 3.4 g of 1-(3-(10,11-dihydro-5H-dibenz[b,f]-azepin-5-yl)-1-propyl)-2-methyl-3-piperidinecarboxylic acid methyl ester as an oil.

To a solution of the above ester (3.4 g, 0.0087 mol) in 96% ethanol (15 ml), 4N sodium hydroxide (4.4 ml) was added and the mixture was stirred at room temperature for 4 h and then left in a refrigerator overnight. Stirring was continued at room temperature for 5 h and 4N hydrochloric acid (6 ml) was added. The solvent was evaporated and the residue was triturated with acetone (30 ml) for 10 minutes. The solid was isolated by filtration, washed with acetone and dried in vacuo. The solid was suspended in a mixture of water (35 ml) and dichloromethane (800 ml). A saturated sodium bicarbonate solution was added until pH 8–9 and when the solid had dissolved. The phases were separated and the aqueous phase was extracted with dichloromethane (250 ml). The organic extracts were combined and the volume was reduced by evaporation. Excess concentrated hydrochloric acid was added and the mixture was evaporated to dryness. The residue was reevaporated twice with dichloromethane and then triturated with acetone. The solid was isolated by filtration and dried in vacuo. This afforded 2.4 g of the title compound as a solid.

M.p. 169°–170° C.

Calculated. for $C_{24}H_{30}N_2O_2$, HCl, H$_2$O: C, 66.59%; H, 7.63%; N, 6.47%. Found: C, 66.64%; H, 7.94%; N, 6.23%.

Example 20

1-(3-(10,11-Dihydro-5H-dibenz[b,f]azepin-5-yl)-1-propyl)-3-quinuclidiniumcarboxylate

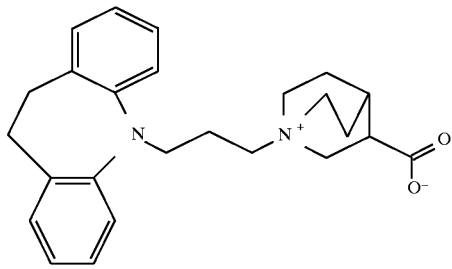

5-(3-Chloropropyl)-10,11-dihydro-5H-dibenzo[b,f]azepine (1.70 g, 6.25 mmol, prepared as described in example 1), and quinuclidine-3-carboxylic acid methyl ester (0.85 g, 5.0 mmol) were dissolved in 2-butanone (25 ml). Dry potassium carbonate (4.15 g, 30 mmol) and sodium iodide (0.75 g, 5 mmol) were added and the stirred mixture was heated at reflux temperature for 5 h. After cooling to room temperature, toluene (25 ml) and water (25 ml) were added. An oily precipitate was formed, which was separated from the solvents by decanting and dissolved in dichloromethane (30 ml). The solution was washed with water (2×30 ml), 1N hydrochloric acid (2×30 ml), saturated sodium hydrogencarbonate solution (30 ml) and water (30 ml). The organic layer was dried over $MgSO_4$. Evaporation in vacuo afforded 1.15 g 1-(3-(10,11-dihydro-5H-dibenz[b,f]azepin-5-yl)-1-propyl)-3-methoxycarbonyl-quinuclidinium hydroxide. The crude product was directly used in the next step without further purification.

The above ester (1.05 g, 2.50 mmol) was dissolved in ethanol (12.5 ml). A 2N solution of sodium hydroxide (4.1 ml, 8.25 mmol) was added and the resulting mixture was stirred at room temperature for 10 minutes. Water (10 ml) was added and ethanol was evaporated in vacuo. The remaining aqueous solution was washed with diethyl ether (2×30 ml) and extracted with 1-butanol (3×20 ml). The butanol phases were washed with water (10 ml) and evaporated in vacuo. Stripping of the remainder with n-heptane (3×20 ml) afforded the title compound (0.71 g) as a foam.

Calculated for $C_{25}H_{30}N_2O_2$, 3.5 $H_2O$: C, 66.20%; H, 8.22%; N, 6.18%; Found: C, 66.52%; H, 8.03%; N, 5.79%.

Example 21

1-(3-(2,8-Dibromo-10,11-dihydro-5H-dibenz[b,f]azepin-5-yl)-1-propyl)-4-piperidinecarboxylic acid hydrochloride

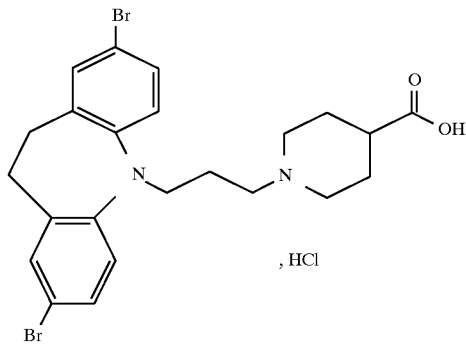

2,8-Dibromo-10,11-dihydro-5H-dibenz[b,f]azepine (1.41 g, 4.0 mmol, prepared according to K. Smith et al., Tetrahedron, 48, 7479 (1992)), was dissolved in toluene (25 ml). Triethylamine (0.60 ml, 4.4 mmol) and 3-chloropropionyl chloride (0.50 ml, 5.2 mmol) were added to the stirred solution at room temperature. Stirring was continued at room temperature for 1 h and at reflux temperature for 2.5 h. The reaction mixture was cooled, filtered and evaporated in vacuo. The crude 3-chloro-1-(2,8-dibromo-10,11-dihydro-5H-dibenz[b,f]azepine-5-yl) propan-1 -one was used in the next step without further purification.

A solution of lithium aluminium hydride (0.326 g, 8.56 mmol) in dry tetrahydrofuran (30 ml) was cooled in an ice bath and concentrated sulphuric acid (0.428 g, 4.28 mmol) was added dropwise. The solution was stirred at room temperature for 0.5 h. A solution of the above product (1.90 g, 4.28 mmol) was added dropwise and stirring was continued for 0.5 h. The reaction was then quenched by careful addition of ethyl acetate (5 ml) followed by water (0.8 ml). Filtration of the mixture and evaporation of the filtrate in vacuo afforded 1.51 g (82%) 2,8-dibromo-5-(3-chloropropyl)-10,11-dihydro-5H-dibenz[b,f]azepine as a foam, which was used in the next step without further purification.

The above chloride (1.5 g, 3.5 mmol) and ethyl isonipecotate (0.79 g, 5.0 mmol) was dissolved in 2-butanone (40 ml). Potassium carbonate (1.4 g, 10 mmol) and potassium iodide (0.43 g, 2.6 mmol) were added and the stirred mixture was heated at reflux temperature for 60 h. The reaction mixture was filtered, the filtrate concentrated in vacuo and the remainder was redissolved in diethyl ether (50 ml). The product was precipitated as the hydrochloride salt by dropwise addition of a 2.6M solution of hydrogen chloride in diethyl ether (2.0 ml, 5.2 mmol). The precipitate was collected by filtration and dried in vacuo, affording 1.3 g (63%) of the 1-(3-(2,8-dibromo-10,11-dihydro-dibenz[b,f]azepin-5-yl)-propyl)-4-piperidine-carboxylic acid ethyl ester hydrochloride as a powder, which was used in the next step without further purification.

The above ester hydrochloride (1.30 g, 2.2 mmol) was dissolved in ethanol (15 ml) and 2N sodium hydroxide (4.0 ml) was added. The solution was stirred for 1.5 h at room temperature, acidified by addition of 1N hydrochloric acid to pH 1 and ethanol was evaporated in vacuo. The aqueous suspension was washed with diethyl ether and filtered. Recrystallisation of the collected solid from ethanol afforded 0.25 g, (19%) of the title compound.

M.p. 165°–166° C.

Calculated for $C_{23}H_{26}N_2Br_2O_2$, HCl, 0.5 $H_2O$, 0.5 $C_2H_6O$: C, 48.79%; H, 5.29%; N, 4.74%; Found: C, 48.64%; H, 5.39%; N, 4.58%.

Example 22

1-(3-(3,7-Dichloro-10,11-dihydro-5H-dibenz[b,f]azepin-5-yl)-1-propyl)-4-piperidinecarboxylic acid hydrochloride.

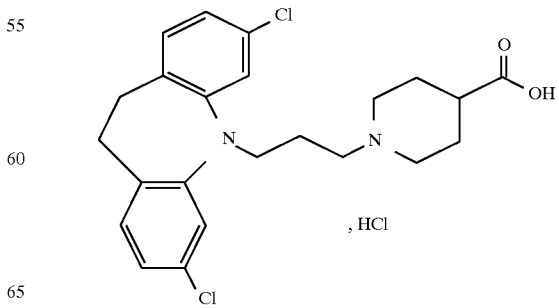

3,7-Dichloro-10,11-dihydro-5H-dibenz[b,f]azepine (4.6 g, 17 mmol) was dissolved in toluene (30 ml) and 3-chloropropionyl chloride (2.3 ml, 24 mmol) was added. The resulting mixture was heated at 90° C. for 3 h, stirred at room temperature for 3 days and heated at 90° C. for 3 h. After cooling, ethyl acetate (150 ml) was added and the mixture was washed with water (2×100 ml). The organic phase was dried (MgSO₄) and evaporated in vacuo. The residue was purified by column chromatography on silica gel (600 ml), using a mixture of ethyl acetate and heptane (1:4) as eluent. This afforded 4.7 g (76%) 3-chloro-1-(3,7-dichloro-10,11-dihydro-5H-dibenz[b,f]azepin-5-yl)-1-propanone as an oil.

TLC: $R_f$=0.14 (SiO₂: ethyl acetate/heptane=1:4)

Lithium aluminum hydride (0.44 g, 11.6 mmol) was dissolved in dry tetrahydrofuran (15 ml) and the solution was cooled to 0° C. Concentrated sulphuric acid (0.31 ml, 5.8 mmol) was slowly and cautiously added using a syringe. The suspension was stirred at room temperature for 0.5 h. A solution of the above amide (2.0 g, 5.8 mmol) in dry tetrahydrofuran (15 ml) was added dropwise to the suspension. The resulting mixture was stirred at room temperature for 1 h. The reaction was quenched by addition of water (1.4 ml), 2N sodium hydroxide (0.5 ml), water (4 ml), and potassium carbonate (5.0 g). The mixture was filtered, and the filter cake was washed with dry tetrahydrofuran. The combined filtrates were evaporated in vacuo to give 1.4 g (69%) 5-(3-chloropropyl)-3,7-dichloro-10,11-dihydro-5H-dibenz[b,f]azepine as an oil.

TLC: $R_f$=0.66 (SiO₂: ethyl acetate/heptane=1:2)

The above chloride (1.3 g, 3.8 mmol) was dissolved in methyl ethyl ketone (20 ml). Potassium iodide (0.63 g, 3.8 mmol), potassium carbonate (3.2 g, 23 mmol), and 4-piperidinecarboxylic acid ethyl ester (1.2 ml, 7.6 mmol) were added, and the resulting mixture was heated at reflux temperature for 24 h. After cooling, ethyl acetate (100 ml) was added and the mixture was washed with water (2×100 ml). The organic phase was dried (MgSO₄) and evaporated in vacuo. The residue was purified by column chromatography on silica gel (600 ml), using a mixture of ethyl acetate and heptane (1:2) as eluent. This afforded 0.84 g (48%) 1-(3-(3,7-dichloro-10,11-dihydro-5H-dibenz[b,f]azepin-5-yl)-1-propyl)-4-piperidinecarboxylic acid ethyl ester as an oil.

TLC: $R_f$=0.22 (SiO₂: ethyl acetate/heptane=1:2)

The above ethyl ester (0.8 g, 1.7 mmol) was dissolved in ethanol (20 ml), and water (10 ml) and 1N sodium hydroxide (1.7 ml) were added. The resulting mixture was stirred at room temperature for 24 h. Water (100 ml) was added and the mixture was washed with diethyl ether (2×60 ml). The pH of the aqueous phase was adjusted to 1 with 5N hydrochloric acid, and the aqueous phase was extracted with dichloromethane (2×100 ml). The combined organic extracts were dried (MgSO₄) and evaporated in vacuo to give an oil. 2-Propanol (15 ml) was added, and the resulting precipitate was filtered off and washed with 2-propanol. Drying in vacuo at 50° C. for 24 h afforded 0.33 g (41%) of the title compound.

M.p. 237°–239° C.

MS(EI) (m/z): 432 (M⁺, 14%), 303 (43%), 142 (100%).

¹H NMR (400 MHz, CDCl₃): $\delta_H$ 1.72–2.02 (m, 5H), 2.48 (m, 1H), 2.85 (m, 2H), 3.05 (m, 2H), 3.08 (s, 4H), 3.39 (m, 2H), 3.80 (t, 2H), 7.03 (dd, 2H), 7.17 (d, 2H), 7.22 (d, 2H).

Example 23

1-(3-(3-Methyl-10,11-dihydro-5H-dibenzo[a,d]cyclohepten-5-ylidene)-1-propyl)-4-piperidinecarboxylic acid hydrochloride

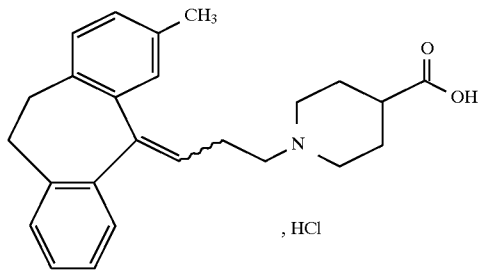

5-(3-Bromo-1-propylidene)-3-methyl-10,11-dihydro-5H-dibenzo[a,d]cycloheptene (1.05 g, 3.3 mmol, prepared as described in WO 9518793) was dissolved in methyl ethyl ketone (20 ml). Potassium iodide (0.44 g, 6.7 mmol), potassium carbonate (2.76 g, 20 mmol), and 4-piperidinecarboxylic acid ethyl ester (0.77 ml, 5.0 mmol) were added and the resulting mixture was heated at reflux temperature for 1 h. After cooling, ethyl acetate (60 ml) was added and the mixture was washed with water (2×60 ml). The organic phase was dried (MgSO₄) and evaporated in vacuo. The residue (1.7 g) was purified by column chromatography on silica gel (600 ml), using a mixture of ethyl acetate and heptane (1:2) as eluent. This afforded 0.97 g (73%) 1-(3-(3-methyl-10,11-dihydro-5H-dibenzo[a,d]cyclohepten-5-ylidene)-1-propyl)-4-piperidinecarboxylic acid ethyl ester as an oil.

TLC: $R_f$=0.20 (SiO₂: ethyl acetate/heptane=1:2)

The above ethyl ester (0.91 g, 1.7 mmol) was dissolved in ethanol (15 ml), and water (5 ml) and 1N sodium hydroxide (2.7 ml) were added. The resulting mixture was stirred at room temperature for 24 h. The reaction mixture was evaporated in vacuo. Water (100 ml) and diethyl ether (70 ml) were added, and the phases were separated. The pH of the aqueous phase was adjusted to 2 with 1N hydrochloric acid, and the aqueous phase was extracted with dichloromethane (3×200 ml). The combined organic extracts were dried (MgSO₄) and evaporated in vacuo to give 0.12 g (13%) of the title compound. More material separated from the acidic aqueous phase on standing. The precipitate was filtered off, washed with water, and dried to give 0.34 g (36%) of the title compound.

M.p.>250° C.

Calculated for C₂₅H₂₉NO₂, HCl: C, 72.89%; H, 7.34%; N, 3.40%. Found: C, 72.65%; H, 7.43%; N, 3.26%.

Example 24

1-(3-(3,7-Dimethyl-10,11-dihydro-5H-dibenz[b,f]azepin-5-yl)-1-propyl)-4-piperidinecarboxylic acid

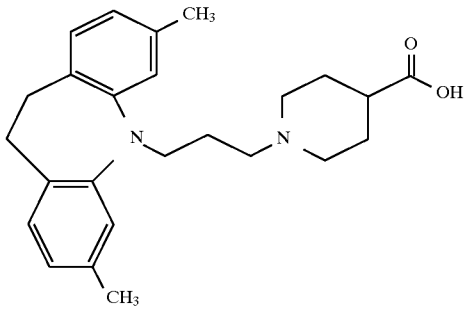

To a solution of 3,7-dimethyl-10,11-dihydro-5H-dibenz[b,f]azepine (6.45 g, 0.029 mol; prepared similarly as described in Brit. Pat. 792615, 1958) and 3-bromo-1-propyl tetrahydro-2-pyranyl ether (8.3 g, 0.037 mol) in dry benzene (80 ml) a suspension of sodium amide (3.2 g, 0.041 mol, 50%wt suspension in toluene) was added. The reaction mixture was heated at reflux temperature for 20 h, allowed to cool, and water (20 ml) was added. The phases were separated, the solvent was evaporated from the organic phase and the residue was dissolved in a mixture of methanol (100 ml) and 5N HCl (30 ml). The mixture was then heated at reflux temperature for 15 minutes, methanol was evaporated and the mixture was extracted with benzene (2×150 ml). The combined organic extracts were dried ($K_2CO_3$), filtered and the solvent was evaporated under vacuum. The residue was purified by chromatography on silica gel (50 g) using first benzene as eluent to separate the starting material. Then, using chloroform as eluent, 2.4 g of 3-(3,7-dimethyl-10,11-dihydro-5H-dibenz[b,f]azepin-5-yl)-1-propanol as an oil was separated.

The above alcohol (2.4 g, 0.0087 mol) was dissolved in benzene (80 ml) and then triethyl amine (3.0 ml) was added. After addition of methane sulfonylchloride (1.3 g, 0.0114 mol) the reaction mixture was stirred for 2 h. Water was added and the phases were separated. The organic phase was dried ($MgSO_4$) and the solvent was evaporated under vacuum. The residue was dissolved in acetone (50 ml). To this solution 4-piperidinecarboxylic acid ethyl ester (2.0 g, 0.0127 mol) and potassium carbonate (3.0 g, 0.0217 mol) were added, and the mixture was heated at reflux temperature for 24 h. The mixture was allowed to cool, then filtered and the solvent was evaporated under vacuum to give a residue, which was further purified by chromatography on silica gel (40 g) using chloroform as eluent. This afforded 2.6 g of 1-(3-(3,7-dimethyl-10,11-dihydro-5H-dibenz[b,f]-azepin-5-yl)-1-propyl)-4-piperidinecarboxylic acid ethyl ester as an oil.

The above ester (2.4 g, 0.057 mol) was dissolved in ethanol (50 ml) and 5 N NaOH (3 ml) was added. The mixture was stirred at 40° C. for 16 h, and ethanol was evaporated under vacuum to give a residue, which was dissolved in water (20 ml). Acetic acid (3 ml) was added to the resulting solution, and the mixture was extracted with dichloromethane (50 ml). The organic extract was dried ($MgSO_4$), and the solvent was evaporated under vacuum. Diethyl ether (50 ml) was added to the residue, affording after filtration and drying 1.85 g (82%) of the title compound as a solid.

M.p. 207°–209° C.

Calculated for $C_{25}H_{32}N_2O_2$, 0.25 $H_2O$: C, 75.63%; H, 8.25%; N, 7.06%; Found: C, 75.58%; H, 8.30%, N, 6.89%.

Example 25

1-(3-(3-Dimethylamino-10,11-dihydro-5H-dibenz[b,f]azepin-5-yl)-1-propyl)-4-piperidinecarboxylic acid

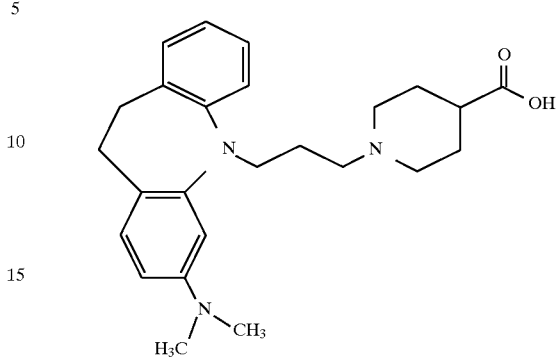

A suspension of sodium amide (2.6 g, 0.033 mol, 50% wt suspension in toluene) was added to a solution of 3-dimethylamino-10,11-dihydro-5H-dibenz[b,f]azepine (6.1 g, 0,0256 mol, prepared similarly as described in Brit. Pat., 1040739,1966) in dry benzene (60 ml). The reaction mixture was heated to 70° C. for 1 h. 3-Bromo-1-propyl-tetrahydro-2-pyranyl ether (7.35 g, 0.033 mol) was added and the mixture was heated at reflux temperature for 20 h. To the cooled reaction mixture, water (20 ml) was added, and the phases were separated. The solvent was evaporated from the organic phase and the residue was dissolved in a mixture of methanol (100 ml) and 5N HCl (30 ml). The mixture was heated at reflux temperature for 15 minutes, and methanol was evaporated. Water (50 ml) was added, pH was adjusted to 8–9 with aqueous ammonia and the mixture was extracted with benzene (2×150 ml). The combined organic extracts were dried ($K_2CO_3$), filtered and the solvent was evaporated under vacuum. The residue, was purified by chromatography on silica gel (50 g) using first benzene as eluent to isolate the starting material. Then, using chloroform as eluent, 3.5 g of 3-(3-di-methylamino-10,11-dihydro-5H-dibenz[b,f]azepin-5-yl)-1-propanol as an oil was isolated.

The above alcohol (3.5 g, 0.0118 mol) was dissolved in benzene (100 ml) and triethylamine (4.0 ml) and methane sulfonylchloride (1.7 9, 0.0148 mol) were added. The reaction mixture was stirred for 2 h. After addition of water, the phases were separated. The organic phase was dried ($MgSO_4$) and the solvent was evaporated under vacuum to give a residue, which was dissolved in acetone (50 ml). To this solution 4-piperidinecarboxylic acid ethyl ester (2.8 g, 0.0178 mol) and potassium carbonate (4.13, 0.03 mol) were added and the mixture was heated at reflux temperature for 24 h. The mixture was allowed to cool, filtered and the solvent was evaporated under vacuum to give a residue, which was further purified by chromatography on silica gel (50 9) using ethyl acetate as eluent. This afforded 3.1 g of 1-(3(3-dimethylamino10,11-dihydro-5H-dibenz[b,f]azepin-5-yl)-1 propyl)-4-piperidinecarboxylic acid ethyl ester as an oil.

The above ester (1.95 g, 0.0045 mmol) was dissolved in ethanol (40 ml) and 5N NaOH (3 ml) was added. The mixture was stirred at 40° C. for 8 h, and ethanol was evaporated under vacuum. The residue was dissolved in water (20 ml). Acetic acid (3 ml) was added to the resulting solution and the mixture was extracted with dichloromethane (50 ml). The organic extract was dried ($MgSO_4$), and the solvent was evaporated under vacuum. Diethyl ether (50 ml) was added to the residue, affording 1.67 g (91%) of the title compound as a solid after filtration and drying.

M.p. 198°–202° C.

Calculated for $C_{25}H_{33}N_3O_2$, 0.25 $H_2O$: C, 72.87%; H, 8.19%; N, 10.20%, Found: C, 72.73%; H, 8.32%; N, 10.00%.

Example 26

(R)-1-(3-(10,11-Dihydro-5H-dibenzo[a,d]cyclohepten-5-ylidene)-1-propyl)-2-piperidinecarboxylic acid hydrochloride.

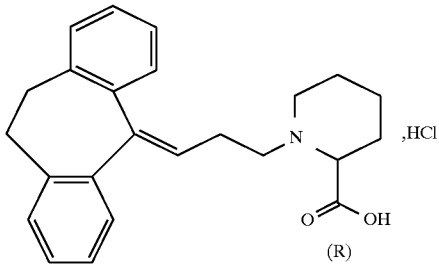

2-Piperidinecarboxylic acid (26 g, 0.201 mol) and (+)-tartaric acid (31.2 g, 0.208 mol) were suspended in a mixture of ethanol (400 ml) and water (25 ml). The mixture was heated to 80° C., and the solution was allowed to cool to room temperature. The precipitated solid was filtered off, washed with ethanol and dried to give 25.4 g (45%) (R)-(+)-2-piperidinecarboxylic acid (+)-tartrate. The mother liquor was evaporated in vacuo, and the residue was dissolved in water (120 ml). A solution of potassium hydroxide (6.5 g, 116 mmol) in water (13 ml) was added, and the precipitated mono potassium tartrate was removed by filtration. Evaporation of the filtrate in vacuo afforded 1 9.5 g crude (S)-(–)-2-piperidinecarboxylic acid.

The above (+)-tartrate (20 g, 72 mmol) was dissolved in water (60 ml) and a solution of potassium hydroxide (4.0 g, 72 mmol) in water (8 ml) was added. The precipitated mono potassium tartrate was removed by filtration and washed with water. The mother liquor was evaporated in vacuo, and the residue was suspended in ethanol (100 ml) and evaporated in vacuo. Suspension in ethanol and evaporation in vacuo was repeated twice. The residue was suspended in ethanol (200 ml), and thionyl chloride (24 ml, 0.28 mol) was added dropwise. The resulting mixture was heated at 70° C. for 2 h, cooled to room temperature and evaporated in vacuo. Diethyl ether (40 ml) and ethanol (1 ml) were added and the suspension was stirred for 30 minutes. The solid was filtered off, washed with diethyl ether and dried to give 11.4 g (82%) of (R)-(+)-2-piperidinecarboxylic acid ethyl ester hydrochloride.

$[\alpha]^{25}_D$=+10.5° (c=4.5% in water)

Gas Chromatography of N-acetyl derivative: $R_t$ =46.4 minutes. Enantiomeric excess=97.9%
(GC was run on a Chrompac CP 9000 Gas Chromatograph with F.I.D. detection using a Chrompac CP-Cyclodextrin capillary column, 25 m long, 0.25 mm internal diameter, using a split flow of 40 ml/min, 180 kPa, a linear gas velocity of 27.6 cm/s, inlet and detector temperatures of 200° C. and a column temperature of 120° C.).

5-(3-Bromo-1-propylidene)-10,11-dihydro-5H-dibenzo[a,d]cycloheptene (2.7 g, 8.6 mmol, prepared as described in WO 9518793), potassium carbonate (7.14 g, 52 mmol), potassium iodide (1.4 g 8.6 mmol), and (R)-(+)-2-piperidine-carboxylic acid ethyl ester hydrochloride (3.3 g, 17 mmol) were mixed in methyl ethyl ketone (50 ml) and heated at reflux temperature for 3 days. After cooling to room temperature, ethyl acetate (100 ml) was added and the mixture was washed with water (2×100 ml). The organic phase was dried ($MgSO_4$) and evaporated in vacuo. The residue was purified by column chromatography on silica gel (600 ml), using a mixture of ethyl acetate and heptane (1:4) as eluent. This afforded 2.62 g (78%) of (R)-1-(3-(10,11-dihydro-5H-dibenzo[a,d]cyclo-hepten-5-ylidene)-1-propyl)-2-piperidinecarboxylic acid ethyl ester as an oil.

TLC: $R_f$=0.28 ($SiO_2$: ethyl acetate/heptane=1:4)

The above ester (2.6 g, 6.7 mmol) was dissolved in a mixture of ethanol (25 ml) and 1,4-dioxane (2 ml). 1N Sodium hydroxide (6.7 ml) was added and the mixture was stirred at room temperature for 16 h. 1N Sodium hydroxide (1.3 ml) was added and the mixture was stirred at room temperature for 4 h. 1N Sodium hydroxide (6.9 ml) and ethanol (10 ml) were added and the mixture was stirred at room temperature for 16 h. 1N Sodium hydroxide (6.9 ml) was added and the mixture was stirred at room temperature for 16 h. 1N Sodium hydroxide (6.7 ml) was added and the mixture was stirred at room temperature for 3 days. Water (100 ml) was added and the mixture was washed with diethyl ether (3×100 ml). The pH of the aqueous phase was adjusted to 1 with 5N hydrochloric acid, and the aqueous phase was extracted with dichloromethane (150 ml). The organic extract was dried ($MgSO_4$) and evaporated in vacuo to give an oil. Acetone (50 ml) was added and the solution was evaporated in vacuo. The acetone treatment was repeated. The solid was suspended in acetone and filtered off. Drying in vacuo at 50° C. for 24 h afforded 1.2 g (51%) of the title compound as an amorphous powder.

MS(EI) (m/z): 316 ($M^+$, 1%), 142 (100%).

$^1$H NMR (400 MHz, $CDCl_3$): $\delta_H$ 1.45–1.75 (m, 5H), 2.1 (m, 1H), 2.4–2.55 (m, 2H), 2.75–3.4 (m, 8H), 3.90 (bs, 1H), 5.80 (t, 1H), 7.05–7.23 (m, 8H).

Example 27

(S)-1-(3-(10,11-Dihydro-5H-dibenzo[a,d]cyclohepten-5-ylidene)-1-propyl)-2-piperidinecarboxylic acid hydrochloride.

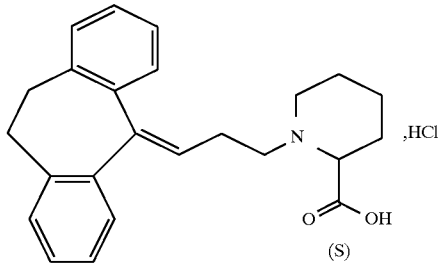

Crude (S)-(–)-2-piperidinecarboxylic acid (19.5 g, prepared as described in example 26) was suspended in ethanol (250 ml), and thionyl chloride (40 ml, 0.46 mol) was added dropwise. After addition was complete, the suspension was heated at reflux temperature for 2 h. The mixture was filtered hot, and the filtrate was cooled to room temperature. Filtration and evaporation in vacuo afforded an oil, which was crystallised by rubbing. Ethanol (10 ml) was added, followed by slow addition of diethyl ether (150 ml). The precipitated solid was filtered off, washed with diethyl ether and dried by suction to give 13.8 g (35% calculated from 2-piperidinecarboxylic acid) (S)-(–)-2-piperidinecarboxylic acid ethyl ester hydrochloride.

$[\alpha]^{25}_D = -10.7°$ (c=4.5% in water)

Gas Chromatography (run as described in example 26) of N-acetyl derivative: $R_t$=47.2 minutes. Enantiomeric excess= 96%.

5-(3-Bromo-1-propylidene)-10,11-dihydro-5H-dibenzo [a,d]cycloheptene (2.7 g, 8.6 mmol, prepared as described in WO 9518793), potassium carbonate (7.14 g, 52 mmol), potassium iodide (1.4 g, 8.6 mmol), and (S)-(-)-2-piperidinecarboxylic acid ethyl ester hydrochloride (3.3 g, 17 mmol) were mixed in methyl ethyl ketone (50 ml) and heated at reflux temperature for 3 days. After cooling to room temperature, ethyl acetate (100 ml) was added and the mixture was washed with water (2×100 ml), dried (MgSO$_4$) and evaporated in vacuo. The residue was purified by column chromatography on silica gel (600 ml), using a mixture of ethyl acetate and heptane (1:4) as eluent. This afforded 2.3 g (69%) of (S)-1-(3-(10,11-dihydro-5H-dibenzo [a,d]cyclohepten-5-ylidene)-1-propyl)-2-piperidinecarboxylicacid ethyl ester as an oil.

TLC: $R_f$=0.22 (SiO$_2$: ethyl acetate/heptane=1:4)

The above ester (2.3 g, 5.9 mmol) was dissolved in a mixture of ethanol (25 ml) and 1,4-dioxane (2 ml). 1N Sodium hydroxide (5.9 ml) was added and the mixture was stirred at room temperature for 16 h. 1N Sodium hydroxide (1.18 ml) was added and the mixture was stirred at room temperature for 4 h. 1N Sodium hydroxide (5.9 ml) was added and the mixture was stirred at room temperature for 16 h. 1N Sodium hydroxide (5.9 ml) was added and the mixture was stirred at room temperature for 16 h. 1N Sodium hydroxide (5.9 ml) was added and the mixture was stirred at room temperature for 3 days. Water (100 ml) was added and the mixture was washed with diethyl ether (3×100 ml). The pH of the aqueous phase was adjusted to 1 with 5N hydrochloric acid, and the aqueous phase was extracted with dichloromethane (150 ml). The organic extract was dried (MgSO$_4$) and evaporated in vacuo to give an oil. Acetone (50 ml) was added and the solution was evaporated in vacuo. The acetone treatment was repeated again. The solid was suspended in acetone, filtered off and dried in vacuo at 50° C. for 24 h to give 0.79 g (37%) of the title compound as an amorphus powder.

MS(EI) (m/z): 362 (M$^+$, 1%), 142 (100%).

$^1$H NMR (400 MHz, CDCl$_3$): $\delta_H$ 1.45–1.75 (m, 5H), 2.1 (m, 1H), 2.4–2.55 (m, 2H), 2.75–3.4 (m, 8H), 3.80 (bs, 1H), 5.80 (t, 1H), 7.05–7.23 (m, 8H

We claim:

1. A compound of formula I

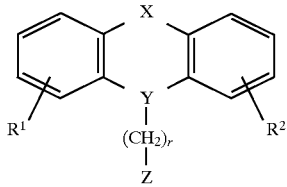

(I)

wherein

R$^1$ and R$^2$ independently are hydrogen, halogen, trifluoromethyl, NR$^6$R$^7$, hydroxy, C$_{1-6}$-alkyl or C$_{1-6}$-alkoxy wherein R$^6$ and R$^7$ independently are hydrogen or C$_{1-6}$-alkyl;

Y is >N—CH$_2$—, wherein only the underscored atom participates in the ring system;

X is —CH$_2$CH$_2$—, —CH$_2$—(C=O)—, —(C=O)—CH$_2$—, or —CH=CH—;

r is 1, 2 or 3; and

Z is selected from

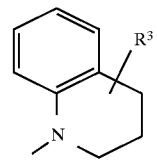

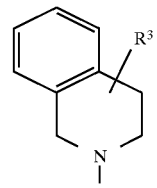

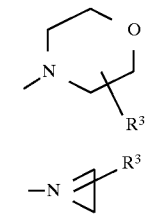

wherein

R$^3$ is —(CH$_2$)$_m$OH or —(CH$_2$)$_p$COR$^4$ wherein m is 0, 1, 2, 3, 4, 5 or 6, p is 0 or 1 and R$^4$ is —OH, —NH$_2$, —NHOH or C$_{1-6}$-alkoxy; or a pharmaceutically acceptable salt thereof.

2. A compound according to claim 1, wherein R$^1$ and R$^2$ independently are hydrogen, halogen, trifluoromethyl, hydroxy, C$_{1-6}$-alkyl or C$_{1-6}$-alkoxy.

3. A compound according to claim 2, wherein X is —CH$_2$CH$_2$—.

4. A compound according to claim 2, wherein Z is

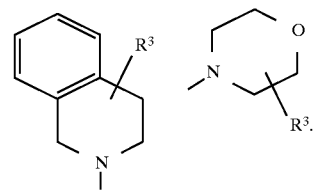

5. A compound according to claim 1 which is:
   4-(3-(10,11-Dihydro-5H-dibenz[b,f]azepin-5-yl)-1-propyl)-2-morpholinecarboxylic acid;
   2-(3-(10,11-Dihydro-5H-dibenz[b,f]azepin-5-yl)-1-propyl)-1,2,3,4-tetrahydro-3-isoquinolinecarboxylic acid;
   1-(3-(10,11-Dihydro-5H-dibenz[b,f]azepin-5-yl)-1-propyl)-2-aziridinecarboxylic acid;
   2-(3-(10,11-Dihydro-5H-dibenz[b,f]azepin-5-yl)-1-propyl)-1,2,3,4-tetrahydro-4-isoquinolinecarboxylic acid; or
a pharmaceutically acceptable salt thereof.

6. A pharmaceutical composition comprising a compound according to claim 1 together with a pharmaceutically carrier or diluent.

7. The pharmaceutical composition according to claim 6, wherein the compound is present in an amount of between 0.5 mg and 1000 mg per unit dose.

8. A method of treating diabetic neuropathy, migraine, neurogenic inflammation, or rheumatoid arthritis in a subject in need of such treatment comprising administering to the subject an effective amount of a compound according to claim 1.

9. A method of treating insulin resistance in a subject in need of such treatment comprising administering to the subject an effective amount of a compound according to claim 1.

10. A method of treating diabetic neuropathy, migraine, neurogenic inflammation, or rheumatoid arthritis in a subject in need of such treatment comprising administering to the subject an effective amount of a pharmaceutical composition according to claim 6.

11. A method of treating insulin resistance in a subject in need of such treatment comprising administering to the subject an effective amount a pharmaceutical composition according to claim 6.

12. A compound of formula I

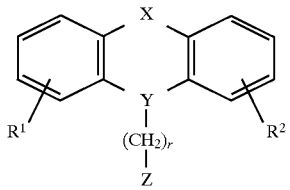

wherein $R^1$ and $R^2$ independently are hydrogen, halogen, trifluoromethyl, $NR^6R^7$, hydroxy, $C_{1-6}$-alkyl or $C_{1-6}$-alkoxy wherein $R^6$ and $R^7$ independently are hydrogen or $C_{1-6}$-alkyl;

Y is >$\underline{N}$—$CH_2$—, wherein only the underscored atom participates in the ring system;

X is —$CH_2CH_2$—, —$CH_2$—(C=O)—, —(C=O)—$CH_2$—, or —CH=CH—;

r is 1, 2 or 3; and

Z is

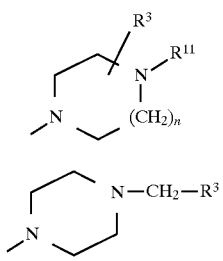

wherein n is 1 or 2; $R^3$ is —$(CH_2)_p COR^4$ wherein p is 0 or 1 and $R^4$ is —OH, —$NH_2$, —NHOH or $C_{1-6}$-alkoxy; and $R^{11}$ is hydrogen or $C_{1-6}$-alkyl; or a pharmaceutically acceptable salt thereof.

13. A compound according to claim 12, wherein $R^1$ and $R^2$ independently are hydrogen, halogen, trifluoromethyl, hydroxy, $C_{1-6}$-alkyl or $C_{1-6}$-alkoxy.

14. A compound according to claim 13, wherein X is —$CH_2CH_2$—.

15. A compound according to claim 12 which is:

4-(3-(10,11-Dihydro-5H-dibenz[b,f]azepin-5-yl)-1-propyl)-2-piperazinecarboxylic acid;

(4-(3-(10,11-Dihydro-5H-dibenz[b,f]azepin-5-yl)-1-propyl)piperazin-1-yl)acetic acid; or a pharmaceutically acceptable salt thereof.

16. A pharmaceutical composition comprising a compound according to claim 12 together with a pharmaceutically carrier or diluent.

17. The pharmaceutical composition according to claim 16, wherein the compound is present in an amount of between 0.5 mg and 1000 mg per unit dose.

18. A method of treating diabetic neuropathy, migraine, neurogenic inflammation, or rheumatoid arthritis in a subject in need of such treatment comprising administering to the subject an effective amount of a compound according to claim 12.

19. A method of treating insulin resistance in a subject in need of such treatment comprising administering to the subject an effective amount of a compound according to claim 12.

20. A method of treating diabetic neuropathy, migraine, neurogenic inflammation, or rheumatoid arthritis in a subject in need of such treatment comprising administering to the subject an effective amount of a pharmaceutical composition according to claim 16.

21. A method of treating insulin resistance in a subject in need of such treatment comprising administering to the subject an effective amount a pharmaceutical composition according to claim 16.

22. (1-(3-(10,11-Dihydro-5H-dibenz[b,f]azepin-5-yl)-1-propyl)-3-piperidinyl)methanol; or a pharmaceutically acceptable salt thereof.

23. 1-(3-(10,11-Dihydro-5H-dibenz[b,f]azepin-5-yl)-1-propyl)-3-quinuclidiniumcarboxylic acid; or a pharmaceutically acceptable salt thereof.

* * * * *